US007947717B2

(12) United States Patent
Pellecchia

(10) Patent No.: US 7,947,717 B2
(45) Date of Patent: May 24, 2011

(54) INHIBITORS OF LETHAL FACTOR PROTEASE

(75) Inventor: Maurizio Pellecchia, San Diego, CA (US)

(73) Assignee: Burnham Institute for Medical Research, La Jolla, CA (US)

( * ) Notice: Subject to any disclaimer, the term of this patent is extended or adjusted under 35 U.S.C. 154(b) by 112 days.

(21) Appl. No.: 12/176,058

(22) Filed: Jul. 18, 2008

(65) Prior Publication Data

US 2010/0016292 A1    Jan. 21, 2010

(51) Int. Cl.
*A61K 31/427* (2006.01)
*C07D 277/04* (2006.01)

(52) U.S. Cl. ...................................... 514/369; 548/183

(58) Field of Classification Search .................. 514/369; 548/183
See application file for complete search history.

(56) References Cited

U.S. PATENT DOCUMENTS

| 4,559,157 | A | 12/1985 | Smith et al. |
| 4,608,392 | A | 8/1986 | Jacquet et al. |
| 4,820,508 | A | 4/1989 | Wortzman |
| 4,938,949 | A | 7/1990 | Borch et al. |
| 4,992,478 | A | 2/1991 | Geria |
| 7,718,680 | B2 | 5/2010 | Pellecchia et al. |
| 2004/0214872 | A1* | 10/2004 | Suto et al. ..................... 514/369 |
| 2005/0187409 | A1 | 8/2005 | Powers et al. |
| 2008/0033025 | A1 | 2/2008 | Pellecchia et al. |

FOREIGN PATENT DOCUMENTS

| WO | WO-00/10573 A1 | 3/2000 |
| WO | WO-2004/093803 A2 | 11/2004 |
| WO | WO 2005/020990 * | 3/2005 ..................... 548/146 |

OTHER PUBLICATIONS

Johnson, Sherida L. Rhodanine Derivatives as Selective Protease Inhibitors Against Bacterial Toxins. Chem. Biol. Drug Des. 71 (2008) 131-139.*
"Table II—FDA-Approved Commercially Marketed Salts", *Remington's Pharmaceutical Sciences*, (17th Edition), Gennaro, A. R., Editor, Mack Publishing Company, Easton, PA 18042, (1985), p. 1418.
Bradley, K. A., et al., "Identification of the Cellular Receptor for Anthrax Toxin", *Nature*, 414, (Nov. 2001), 225-229.
Boulamwini, J. K., et al., "CoMFA and CoMSIA 3D QSAR and Docking Studies on Conformationally-Restrained Cinnamoyl HIV-1 Integrase Inhibitors: Exploration of a Binding Mode at the Active Site", *Journal of Medicinal Chemistry*, 45, (2002), 841-852.
Bush, B. L., et al., "Sample-Distance Partial Least Squares: PLS Optimized for Many Variables, With Application to CoMFA", *Journal of Computer-Aided Molecular Design*, 7(5), (Oct. 1993), 587-619.
Cornell, W. D., "A Second Generation Force Field for the Simulation of Proteins, Nucleic Acids, and Organic Molecules", *Journal of the American Chemical Society*, 117(19), (1995), 5179-5197; (Additions and Corrections, *Journal of the American Chemical Society*, 118(9), (1996), 2309-2310.
Cramer, III, R. D., et al., "Comparative Molecular Field Analysis (CoMFA). 1. Effect of Shape on binding of Steroids to Carrier Proteins", *Journal of the American Chemical Society*, 110(18), (1988), 5959-5967.
Dalvit, C., et al., "A General NMR Method for Rapid, Efficient, and Reliable Biochemical Screening", *Journal of American Chemical Society*, 125(47), (2003), 14620-14625.
Duesbery, N. S., et al., "Proteolytic Inactivation of MAP-Kinase-Kinase by Anthrax Lethal", *Science*, 280(5364), (May 1, 1998), 734-737.
Forino, M., et al., "Efficient Synthetic Inhibitors of Anthrax Lethal Factor", *Proc. Natl. Acad. Sci., USA*, 102(27), (Jul. 5, 2005), 9499-9504.
Hajduk, P. J., et al., "One-Dimensional Relaxation- and Diffusion-Edited NMR Methods for Screening Compounds That Bind to Macromolecules", *Journal of American Chemical Society*, 119(50), (1997),12257-12261.
Hanna, P., "Anthrax Pathogenesis and Host Response", *Current Topics in Microbiology and Immunology*, vol. 225, (1998), 13-35.
Hanna, P. C., et al., "On the Role of Macrophages in Anthrax", *Proc. Natl. Acad. Sci. USA*, 90, (1993),10198-10201.
Huffman, M. A., et al., "Lithium Alkoxides of Cinchona Alkaloids as Chiral Controllers for Enantioselective Acetylide Addition to Cyclic N-Acyl Ketimines", *Journal of Organic Chemistry*, 60, (1995), 1590-1594.
Jahnke, W., et al., "Spin Label Enhanced NMR Screening", *Journal of American Chemical Society*, 123(13), (2001), 3149-3150.
Jones, G., et al., "Development and Validation of a Genetic Algorithm for Flexible Docking", *Journal of Molecular Biology*, 267(3), (1997), 727-748.
Jozwiak, K., et al., "Interaction of Noncompetitive Inhibitors With an Immobilized α3β4 Nicotinic Acetylcholine Receptor Investigated by Affinity Chromaqtography, Quantitative-Structure Activity Relationship Analysis, and Molecular Docking", *Journal of Medicinal Chemistry*, 47, (2004), 4008-4021.
Lacova, M., et al., "Effect of Microwave Irradiation on the Condensation of 6-Substituted 3-Formylchromones With Some Five-Membered Heterocyclic Compounds", *Molecules*, 5, (2000),167-178.
Leppla, S. H., "Anthrax Toxin Edema Factor: A Bacterial Adenylate Cyclase That Increases Cyclic AMP Concentrations in Eukaryotic Cells", *Proc. Natl. Acad. Sci. USAA*, 79, (May 1982), 3162-3166.
Madhavan, G. R., et al., "Synthesis and Biological Activity of Novel Pyrimidinone Containing Thiazolidinedione Derivatives", *Bioorganic & Medicinal Chemistry*, 10, (2002), 2671-2680.
Madkour, H. M., et al., "Behavior of Some Activated Nitriles Toward Barbituric Acid, Thiobarbituric Acid and 3-Methyl-1-Phenylpyrazol-5-one", *Molecules*, 5, (2000), 746-755.

(Continued)

*Primary Examiner* — Susannah Chung
*Assistant Examiner* — Samantha L Shterengarts
(74) *Attorney, Agent, or Firm* — Schwegman, Lundberg & Woessner, P.A.

(57) ABSTRACT

The invention provides compounds that can efficiently and specifically inhibit bacterial toxins, such as inhibit the lethal factor (LF) protease activity of anthrax toxin and/or botulinum neurotoxin type A. The invention also provides methods for inhibiting proteases, such as lethal factor protease, as well as methods for treating bacterial infections, such as anthrax and botulinum.

5 Claims, 4 Drawing Sheets

OTHER PUBLICATIONS

Mayer, M., et al., "Characterization of Ligand Binding by Saturation Transfer Difference NMR Spectroscopy", *Angew. Chem. International Edition*, 38(12), (1999), 1784-1788.

Meyer, B., et al., "NMR Spectroscopy Techniques for Screening and identifying Ligand Binding to Protein Receptors", *Angew. Chem. International Edition*, 42(8), (2003), 864-890.

Pan, D., et al., "Constructing Optimum Blood Brain Barrier QSAR Models Using a Combination of 4D-Molecular Similarity Measures and Cluster Analysis", *Journal of Chemical Information and Computer Science*, 44, (2004), 2083-2098.

Park, J. M., et al., "Macrophage Apoptosis by Anthrax Lethal Factor Through p38 MAP Kinase Inhibition", *Science*, 297(5589), (Sep. 20, 2002), 2048-2051.

Pellecchia, M., et al., "NMR in Drug Discovery", *Nature Reviews*, 1(3), (Mar. 2002), 211-219.

Pellecchia, M., et al., "NMR-Based Structural Characterization of Large Protein-Ligand Interactions", *Journal of Biomolecular NMR*, 22, (2002), 165-173.

Pellizzari, R., et al., "Anthrax Lethal Factor Cleaves MKK3 in Macrophages and Inhibits the LPS/IFNγ-induced Release of NO and TNFα", *FEBS Letters*, 462(1-2), (Nov. 26, 1999), 199-204.

Petosa, C., et al., "Crystal Structure of the Anthrax Toxin Protective Antigen", *Nature*, 385, (Feb. 1997), 833-838.

Schwarze, S. R., et al., "Protein Transduction: Unrestricted Delivery Into All Cells?", *Trends in Cell Biology*, 10(7), (Jul. 1, 2000), 290-295.

Schymkowitz, J. W. H., et al., "Prediction of Water and Metal Binding Sites and Their Affinities by Using the Fold-X Force Field", *Proc. Natl. Acad. Sci. USA*, 102(29), (Jul. 19, 2005), 10147-10152.

Scobie, H. M., et al., "Human Capillary Morphogenesis Protein 2 Functions as an Anthrax Toxin Receptor", *Proc. Natl. Acad. Sci. USA*, 100(9), (Apr. 29, 2003), 5170-5174.

Sellman, B. R., et al., "Dominant-Negative Mutants of a Toxin Subunit: An Approach to Therapy of Anthrax", *Science*, 292, (Apr. 27, 2001), 695-697.

Smith, H., et al., "Observations on Experimental Anthrax: Demonstration of a Specific Lethal Factor Produced in vivo by *Bacillus anthracis*", *Nature*, 173(4410), (May 8, 1954), 869-870.

Stennicke, H. R., et al., "Caspases: Preparation and Characterization", *Methods: A Companion to Methods in Enzymology*, 17, (1999), 313-319.

Stewart, J. J., "Optimization of Parameters for Semiempirical Methods I. Method", *Journal of Computational Chemistry*, 10(2), (1989), 209-220.

Teschner, M., et al., "Texture Mapping: A New Tool for Molecular Graphics", *Journal of Molecular Graphics*, 12(2), (1994), 98-105.

Tucker, T. J., et al., "Synthesis of a Series of 4-(Arylethynyl)-6-chloro-4-cyclopropyl-3,4-dihydroquinazolin-2(1H)-ones as Novel Non-nucleoside HIV-1 Reverse Transcriptase inhibitors", *Journal of Medicinal Chemistry*, 37, (1994), 2437-2444.

Vitale, G., et al., "Anthrax Lethal Factor Cleaves the N-Terminus of MAPKKs and Induces Tyrosine/Threonine Phosphorylation of MAPKs in Cultured Macrophages", *Biochemical and Biophysical Research Communications*, 248(3), (1998), 706-711.

Vitale, G., et al., "Susceptibility of Mitogen-Activated Protein Kinase Kinase Family Members to Proteolysis by Anthrax Lethal Factor", *Thd Biochemical Journal.*, 352(3), (2000), 739-745.

Wang, G.-W., et al., "Solvent-Free and Aqueous Knoevenagel Condensation of Aromatic Ketones With Malononitrile", *ARKIVOC*, vol. 2004, Part (ix), (2004), 4-8.

Zhou, Z., et al., "CoMFA 3D-QSAR Analysis of HIV-1 RT Non-nucleoside Inhibitors, TIBO Derivatives Based on Docking Conformation and Alignment", *Journal of Chemical Information and Computer Science*, 44(6), (2004), 2167-2178.

"U.S. Appl. No. 12/699,082, Non-Final Office Action mailed Sep. 17, 2010", 7 pgs.

* cited by examiner

INHIBITORS OF LETHAL FACTOR PROTEASE

GOVERNMENT SUPPORT

This invention was made with government support under Grant Numbers AI070494 and AI055789 awarded by the National Institutes of Health. The United States Government has certain rights in the invention.

BACKGROUND OF THE INVENTION

The development of new biodefense therapeutics against anthrax and botulinum neurotoxins (BoNT) has heightened with the recent threat of these agents being used as biological weapons. Lethal factor (LF), a component of the anthrax tripartite exotoxin, cleaves mitogen-activated protein kinase kinases (MAPKK; 1-3) thus disrupting signal transduction leading to macrophage lysis (4). Following inhalation of anthrax spores, spores can adhere to alveolar macrophages and subsequently germinate. Bacteria migrate to lymph nodes where they rapidly multiply and excrete the anthrax exotoxin composed of protective antigen (PA; 83 kDa), LF, and calmodulin-activated edema factor adenylate cyclase (EF; 89 kDa). To exert its lethal effect, LF must enter inside the cell compartment. This is mediated by PA that binds to cellular receptors and, following its proteolytic activation by the furin-like proprotein convertases and the release of the N-terminal 20-kDa fragment, generates the mature PA protein (PA63). Finally, PA63 heptamerizes and binds both LF and EF. Following endocytosis of the resulting complexes, the engulfed molecules of LF and EF are liberated and exert their toxic action.

Botulinium neurotoxins, represent even more dreadful bioterrorism agents, because BoNTs may be delivered by aerosol (7, 8). With the increased use of BoNTs in physical/cosmetic ailments (8-13), the potential misuse of these toxins is worrisome (14). Currently, the only available treatment once BoNT has invaded the nervous system is critical care mechanical ventilation (14). However, the effects of internalized BoNTs can last for months (15) in which mechanical ventilation is an intolerable burden for those affected (14). Botulinum neurotoxins are composed of a heavy chain (HC) and a light chain (LC) which is connected by a disulfide bridge (16). The HC binds to neurons which transports the LC into the cytosol (17). The LC is a zinc metalloprotease, similar to anthrax that cleaves neuronal proteins involved in the neurotransmitter release. There are seven serotypes (BoNT A-G) involved in the cleavage of a component of the soluble NSF-ethylmaleimide-sensitive factor attachment protein receptor proteins (18), which mediates the exocytosis of acetylcholine into neuromuscular junctions (14). Both BoNT serotypes A and E cleave SNAP-25 [synaptosomal-associated protein (25 KDa)] (19), while serotypes B, D, F, and G cleave vesicle-associated membrane protein (20-23) and serotype C cleaves both SNAP25 and syntaxin 1 (14, 24).

The lethal action of anthrax toxin can be neutralized at several stages during its entry into the cell. In fact, it would be possible to inhibit PA63 processing, pore assembly or binding to receptor; moreover a successful therapeutic treatment could prevent LF or EF binding or their translocation into the cytosol (Sellman, B. R., Mourez, M., Collier, R. J. *Science* 292, 695-697 (2001)). Nevertheless inhibition of LF protease activity is still the most promising avenue for this harmful disease (Schwarze, S. R., Hruska, K. A., Dowdy, S. F. *Trends Cell Biol.* 10, 290-295 (2000)).

Inhibition of LF protease activity is believed to be a promising avenue for this harmful disease (Schwarze, S. R., Hruska, K. A., Dowdy, S. F. *Trends Cell Biol.* 10, 290-295 (2000)). Thus, a continuing need exists for compounds that inhibit lethal factor (LF) protease activity of anthrax toxin.

SUMMARY

The present invention provides compounds that can efficiently and specifically inhibit lethal factor (LF) protease activity of anthrax toxin. Accordingly, the invention provides compounds of formula I and a therapeutic method for inhibiting lethal factor protease activity comprising administering an effective inhibitory amount of a compound of formula I:

(I)

wherein
$R^1$ is phenyl, pyridyl, or thiophenyl optionally substituted with 1, 2, or 3 substituents independently selected from halo, $C_{1-3}$alkyl, $C_{1-3}$alkoxy, (aryl)$C_{1-3}$alkoxy optionally substituted with halo, $-CF_3$, $-NO_2$, $-CO_2H$, $-SO_2NH_2$, $-SO_2NR^xR^y$ wherein $R^x$ and $R^y$ taken together with the nitrogen to which they are attached form a morpholino or piperidino group, or an ortho fused tetrahydrofuran optionally substituted with $C_{1-3}$alkyl;
$R^2$ is $-(CH_2)_{1-3}CO_2H$, $-(CH_2)_{1-3}SO_3H$, or heterocycle; wherein any $CH_2$ or heterocycle of $R^2$ is optionally substituted with 1 or 2 substituents independently selected from halo, $-OR^a$, $-NO_2$, $-NH_2$, $-SO_2NH_2$, $-CO_2H$, $-CONH_2$, $-CO_2CH_3$, $-OCF_3$, or $-CF_3$; wherein $R^a$ is hydrogen, or $C_{1-4}$alkyl; and
$R^3$ is H or phenyl optionally substituted with 1-5 halo groups;
or a pharmaceutical acceptable salt thereof.

Additionally, the invention provides compounds of formula II and a therapeutic method for inhibiting lethal factor protease activity comprising administering an effective inhibitory amount of a compound of formula II:

(II)

wherein
$R^1$ is hydrogen, or phenyl optionally substituted with 1, 2, or 3 substituents independently selected from alkyl, halo, $-NO_2$, $-CO_2H$, or $-SO_2NH_2$;
----- optionally forms a double bond;
$A^1$ and $A^2$ are each independently CH, C when substituted, or N;
$A^3$ is S or NH;
$R^2$ is hydrogen, $-C_{1-4}$alkyl, $-C_{1-4}$alkenyl, $-CO_2H$, $-(CH_2)_{1-3}CO_2H$, $C_{1-6}$alkoxycarbonyl, furyl, furyl$C_{1-3}$alkylene-, phenyl, (phenyl)$C_{1-3}$alkylene-, or (pyridyl)$C_{1-3}$alkylene-;

wherein the alkyl or phenyl groups of $R^2$ are optionally substituted with 1, 2, or 3 substituents independently selected from halo, $-OR^a$, $-NO_2$, $-NH_2$, $-SO_2NH_2$, $-CO_2H$, $-CONH_2$, $-CO_2CH_3$, $-OCF_3$, or $-CF_3$; wherein $R^a$ is hydrogen, or $C_{1-4}$alkyl;

or a pharmaceutical acceptable salt thereof

The invention also provides compounds of formula III and a therapeutic method for inhibiting lethal factor protease activity comprising administering an effective inhibitory amount of a compound of formula III:

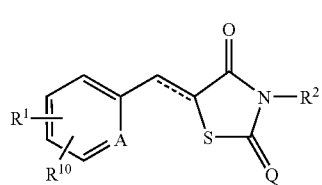

(III)

wherein $R^1$ and $R^{10}$ are each independently hydrogen, halo, heterocycle, phenyl, or a heterocycle substituted N—H or N-alkyl aminoalkoxy group; or $R^1$ and $R^{10}$ together form an ortho-fused aryl, heteroaryl, or heterocyclic ring;

wherein any heterocycle, heteroaryl, or aryl of $R^1$ and $R^{10}$ is optionally substituted with 1, 2, or 3 substituents independently selected from alkyl, halo, $-NO_2$, $-CO_2H$, or $-SO_2NH_2$;

A is CH, C when substituted, or N;

Q is O or S; and

----optionally forms a double bond;

$R^2$ is hydrogen, $-C_{1-4}$alkyl, $-C_{1-4}$alkenyl, $-CO_2H$, $-(CH_2)_{1-3}CO_2H$, $-(CH_2)_{1-3}SO_3H$, $-(CH_2)_{1-3}SO_2NH_2$, $C_{1-6}$alkoxycarbonyl, furyl, furyl$C_{1-3}$alkylene-, phenyl, (phenyl)$C_{1-3}$alkylene-, or (pyridyl)$C_{1-3}$alkylene-;

wherein any alkyl or phenyl group of $R^2$ is optionally substituted with 1, 2, or 3 substituents independently selected from halo, $-NO_2$, $-NH_2$, $-SO_2NH_2$, $-CO_2H$, $-CONH_2$, $-CO_2CH_3$, $-CF_3$, $-OCF_3$, or $-OR^b$, wherein $R^b$ is hydrogen, or $C_{1-4}$alkyl;

or a pharmaceutical acceptable salt thereof.

Additionally, the invention provides compounds of formula IV and a therapeutic method for inhibiting lethal factor protease activity comprising administering an effective inhibitory amount of a compound of formula IV:

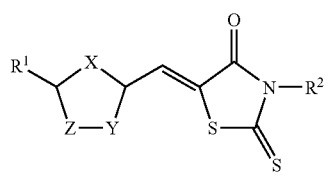

(IV)

wherein $R^1$ is hydrogen, or phenyl optionally substituted with 1, 2, or 3 substituents independently selected from alkyl, halo, $-NO_2$, $-CO_2H$, or $-SO_2NH_2$;

X, Y and Z are each independently O, S, —NH—, $-CH_2-$, $=CH-$, or $=N-$; and $R^2$ is $-(CH_2)_{1-3}SO_3H$, $-(CH_2)_{1-3}$heterocycle, or heterocycle;

wherein any $CH_2$ or heterocycle group of $R^2$ is optionally substituted with 1 or 2 substituents independently selected from halo, $-NO_2$, $-NH_2$, $-SO_2NH_2$, $-CO_2H$, $-CONH_2$, $-CO_2CH_3$, $-OCF_3$, $-CF_3$, or $-OR^a$, wherein $R^a$ is hydrogen, or $C_{1-4}$alkyl;

or a pharmaceutical acceptable salt thereof.

The invention further provides compounds of formula V and a therapeutic method for inhibiting lethal factor protease activity comprising administering an effective inhibitory amount of a compound of formula V:

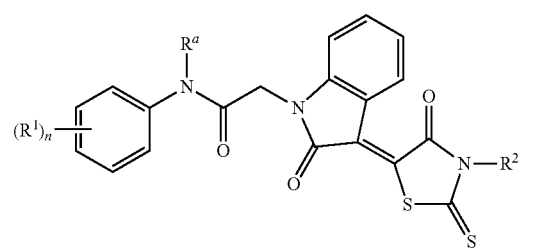

(V)

wherein each $R^1$ is independently hydrogen, alkyl, alkoxy, halo, haloalkyl, hydroxy, hydroxyalkyl, aryl, heteroaryl, heterocycle, cycloalkyl, alkanoyl, alkoxycarbonyl, amino, alkylamino, acylamino, nitro, trifluoromethyl, trifluoromethoxy, carboxy, carboxyalkyl, alkylthio, alkylsulfinyl, alkylsulfonyl, or cyano;

n is 1, 2, 3, 4, or 5;

$R^a$ is hydrogen or $C_{1-4}$alkyl;

$R^2$ is hydrogen, $-C_{1-4}$alkyl, $-C_{1-4}$alkenyl, $-CO_2H$, $-(CH_2)_{1-3}CO_2H$, $-(CH_2)_{1-3}SO_3H$, $-(CH_2)_{1-3}SO_2NH_2$, $C_{1-6}$alkoxycarbonyl, furyl, furyl$C_{1-3}$alkylene-, phenyl, (phenyl)$C_{1-3}$alkylene-, or (pyridyl)$C_{1-3}$alkylene-; and wherein any alkyl or phenyl group of $R^2$ is optionally substituted with 1, 2, or 3 substituents independently selected from halo, $-NO_2$, $-NH_2$, $-SO_2NH_2$, $-CO_2H$, $-CONH_2$, $-CO_2CH_3$, $-CF_3$, $-OCF_3$, or $-OR^b$, wherein Rb is hydrogen, or $C_{1-4}$alkyl;

or a pharmaceutical acceptable salt thereof.

Additionally, the invention provides compounds of formula VI and a therapeutic method for inhibiting lethal factor protease activity comprising administering an effective inhibitory amount of a compound of formula VI:

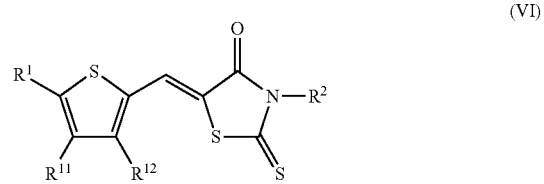

(VI)

wherein

R$^1$ is halo, heterocycle, heteroaryl, or

[Structure: thiazolidinone derivative with CH=, C=O, CO$_2$H, N, S, and =S groups]

R$^2$ is hydrogen, —C$_{1-4}$alkyl, —C$_{1-4}$alkenyl, —CO$_2$H, —(CH$_2$)$_{1-3}$CO$_2$H, C$_{1-6}$alkoxycarbonyl, furyl, furylC$_{1-3}$alkylene-, phenyl, (phenyl)C$_{1-3}$alkylene-, or (pyridyl)C$_{1-3}$alkylene-;

wherein the alkyl or phenyl groups of R$^2$ are optionally substituted with 1, 2, or 3 substituents independently selected from halo, —NO$_2$, —NH$_2$, —SO$_2$NH$_2$, —CO$_2$H, —CONH$_2$, —CO$_2$CH$_3$, —CF$_3$, —OCF$_3$, or —OR$^a$, wherein R$^a$ is hydrogen or C$_{1-4}$alkyl;

R$^{11}$ and R$^{12}$ are each H or R$^{11}$ and R$^{12}$ taken together form an ethylenedioxy group;

or a pharmaceutical acceptable salt thereof.

Additionally, the invention provides compounds of formula VII and a therapeutic method for inhibiting lethal factor protease activity comprising administering an effective inhibitory amount of a compound of formula VII:

[Structure (VII): bicyclic compound with X, Y, Z, R$^1$, R$^2$, N, S, and C=O, =S groups]

(VII)

wherein
R$^1$ is hydrogen, —C$_{1-4}$alkyl, or phenyl;
wherein X, Y and Z are a combination of O, S, —NH—, —CH$_2$—, =CH—, or =N—;
X is —S— or =N—;
Y is —O— or —C— substituted by C$_{1-4}$alkyl or heterocycle;
Z is —O—, —S—, =N—, or —C— substituted by heterocycle;
the ring containing X, Y, and Z is aromatic and includes two double bonds, and one of X, Y, or Z comprises a carbon atom;
R$^2$ is hydrogen, —C$_{1-4}$alkyl, —C$_{1-4}$alkenyl, —CO$_2$H, —(CH$_2$)$_{1-3}$CO$_2$H, C$_{1-6}$alkoxycarbonyl, furyl, furylC$_{1-3}$alkylene-, phenyl, (phenyl)C$_{1-3}$alkylene-, or (pyridyl)C$_{1-3}$alkylene-;
wherein the alkyl or phenyl groups of R$^2$ are optionally substituted with 1, 2, or 3 substituents independently selected from halo, —NO$_2$, —NH$_2$, —SO$_2$NH$_2$, —CO$_2$H, —CONH$_2$, —CO$_2$CH$_3$, —CF$_3$, —OCF$_3$, or —OR$^a$, wherein R$^a$ is hydrogen or C$_{1-4}$alkyl;
or a pharmaceutical acceptable salt thereof.

Accordingly, the invention provides compounds of formulas I-VII and methods of treatment using compounds of formulas I-VII. One method of treatment includes inhibiting bacterial toxins. The bacterial toxin can be, for example, anthrax lethal factor and/or BoNT/A. Another method of treatment includes inhibiting a metalloprotease. The metalloprotease can be a human matrix metalloprotease, such as MMP-2 and/or MMP-9. The invention further provides a method for preventing or inhibiting lethal factor-induced cell death of macrophages. Additionally, the invention provides methods for treating and/or inhibiting anthrax or botulinium infections. The treating or inhibiting can include administering an effective inhibitory amount of a compound of any one of formulas I-VII, and/or contacting a patient, cell, or group of cells with an effective amount of a compound of any one of formulas I-VII.

In some embodiments of the invention, the compound of any one of formulas I-VII can be used to prepare a composition that includes a pharmaceutically acceptable diluent or carrier, optionally in combination with an antibacterial agent. The antibacterial agent can be ciprofloxacin (commonly referred to as cipro). Accordingly, the invention also provides methods of treatment that include the use of a compound of any one of formulas I-VII in combination with an antibacterial agent, such as ciprofloxacin.

The invention further provides compounds that inhibit LF protease activity in in vitro assays. Accordingly, a therapeutic method is provided for treating a mammal in need of inhibition on LF protease activity, by administering an effective inhibitory amount of a compound of any one of formulas I-VII. In one embodiment the mammal is human. The invention also provides a therapeutic method to inhibit lethal factor (LF) protease activity of anthrax toxin comprising contacting the cell, in vitro or in vivo, with an effective amount of a compound of a formula described herein.

The invention also provides a compound of a formula described herein for use in medical therapy, in some embodiments for use in treating lethal factor (LF) protease activity of anthrax toxin, as well as the use of a compound of a formula described herein for the manufacture of a medicament for the treatment of a pathological condition or symptom in a mammal, such as a human, which is associated with lethal factor (LF) protease activity from anthrax.

The invention also provides a method of identifying an agent that inhibits the lethal factor (LF) protease activity of anthrax toxin, comprising: a) identifying detecting a selective lethal factor (LF) protease inhibitor; b) contacting a bound lethal factor (LF) protease inhibitor with a test compound, said test compound suspected of being able to inhibit lethal factor (LF) protease; and c) detecting dissociation of said lethal factor (LF) protease inhibitor from said labeled BCl-X$_L$, whereby said candidate agent is identified as an agent that inhibits BCl-X$_L$. The invention provides novel compounds as described herein, such as compounds included in any one of formulas I-VII.

The invention also provides novel intermediates for the synthesis of compounds of formulas I-VII, as well as methods of preparing compounds formulas I-VII. The invention also provides compounds of formulas I-VII that are useful as intermediates for the synthesis of other useful compounds. The compounds and compositions can also be used to prepare a medicament to treat a diseases in a mammal, for example, anthrax disease in a human.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description. The description and accompanying drawings may highlight a certain specific example, or a certain aspect of the invention, however, one skilled in the art will understand that portions of the example or aspect may be used in combination with other examples or aspects of the invention, and that that portions of the example or aspect may be excluded from other examples or aspects of the invention.

DETAILED DESCRIPTION

Figure 1A:
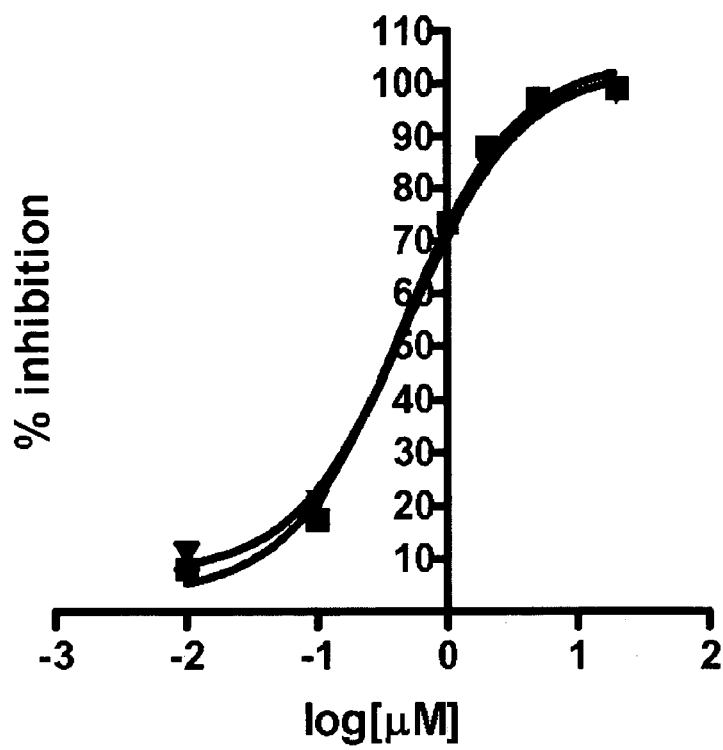
FIG. 1: Kinetics of inhibition of lethal factor (LF) for compounds 9 and 13. $IC_{50}$ evaluation of (A) compound 9 and (B) compound 13 against LF in the absence (squares) and presence (triangles) of PA63; $K_i$ evaluation of compound 9 (C) measured at various concentration of inhibitor (top line, 5 µM; middle line, 3 µM; bottom line, no inhibitor) and compound 13 (D) measured at various concentrations of inhibitor (top line, 1 µM; middle line, 0.5 µM; bottom line, no inhibitor).
Figure 1B:
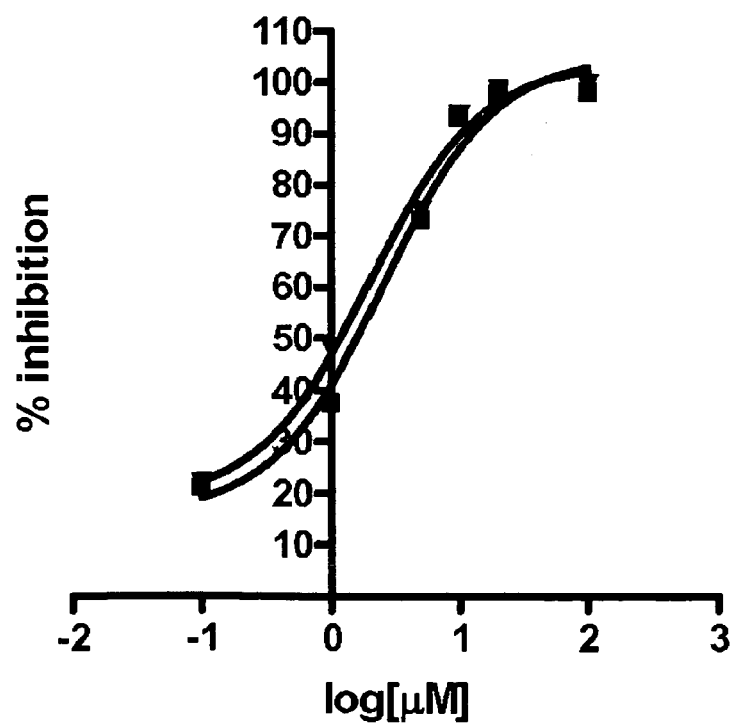
Figure 1C:
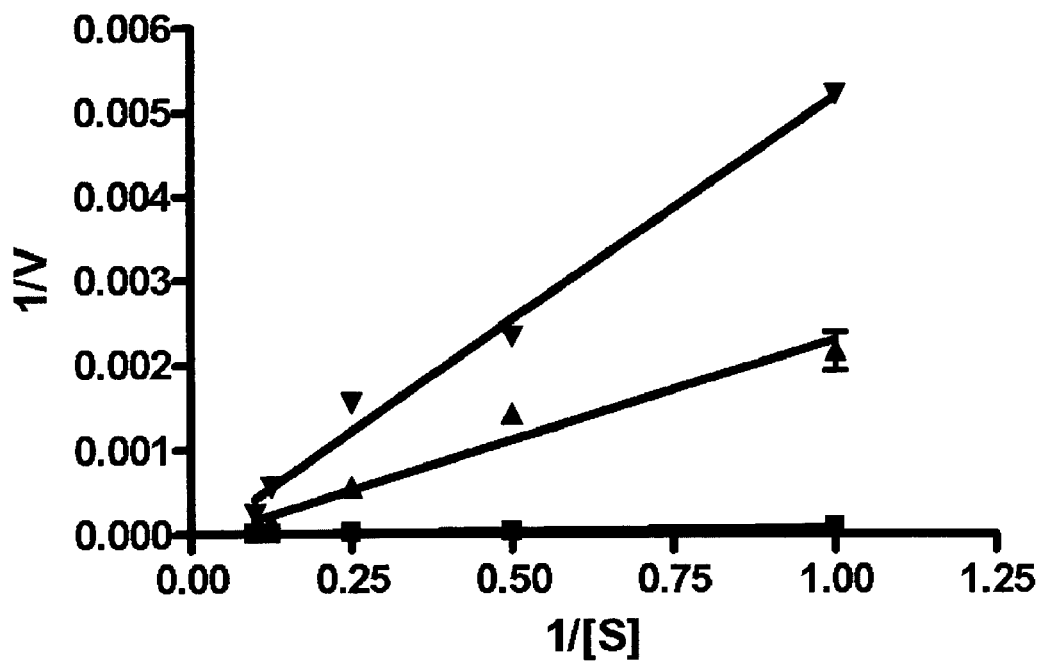
Figure 1D:
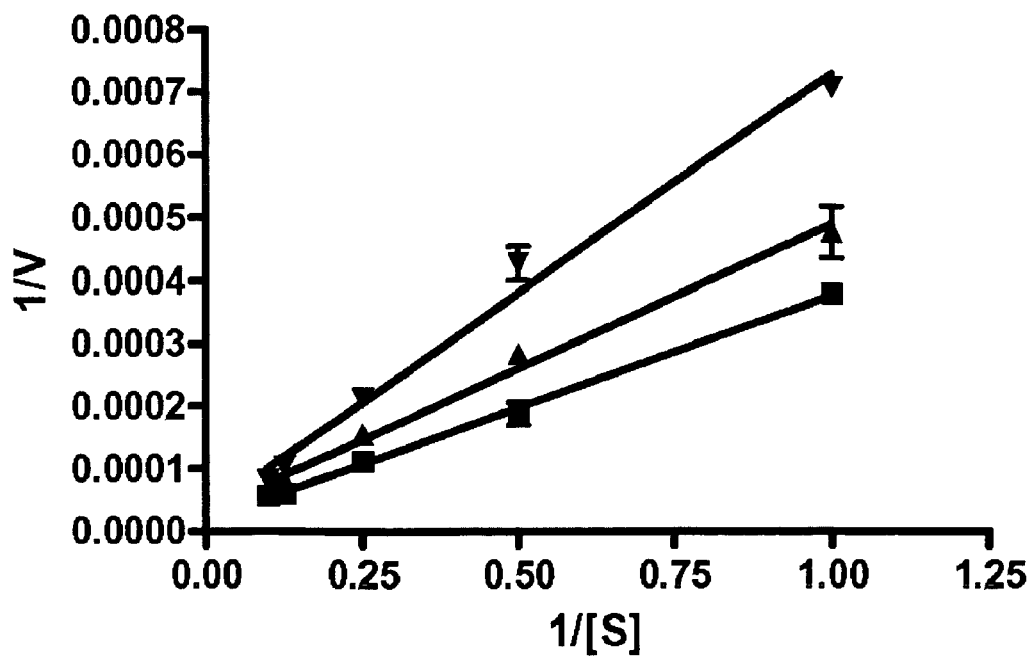
Figure 2A:
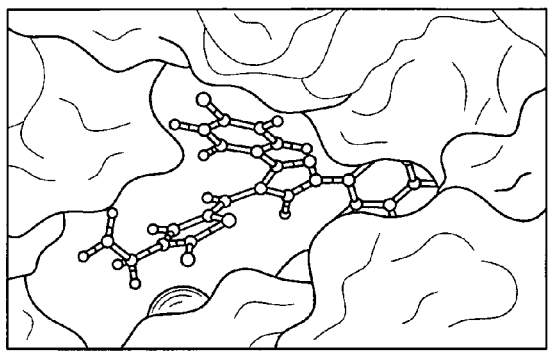
FIG. 2: Molecular docking studies. Stereo views of the molecular model of compound 34 docked into the catalytic pockets of BoNT A (PDB-ID 2G7N; A and B) or lethal factor (PDB-ID 1YQY; C and D). For both targets, the protein surface was generated with MOLCAD and the $Zn^{2+}$ ion is shown as a sphere.
Figure 2B:
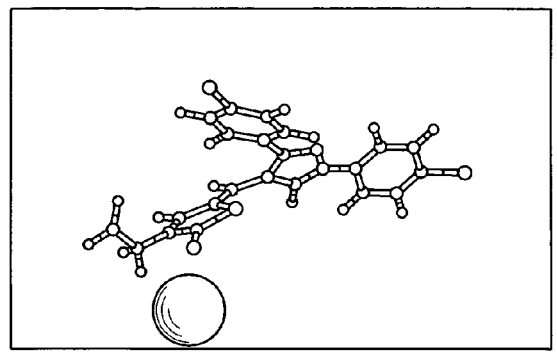
Figure 2C:
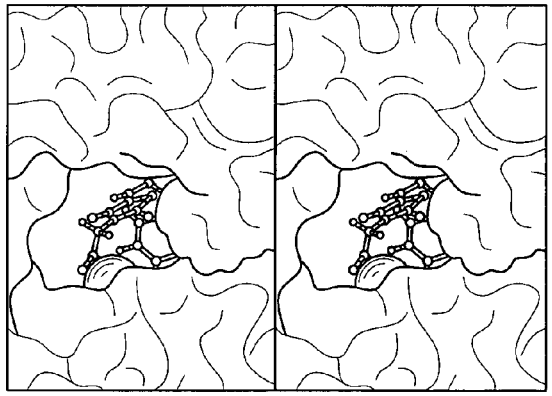
Figure 2D:
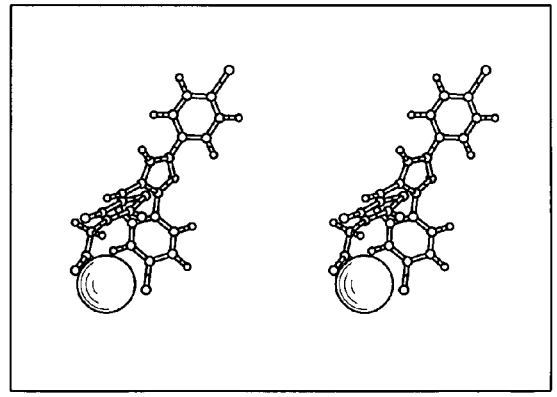

New compounds and methods have been developed that inhibit LF and provide significant protection against *Bacillus anthracis*. The compounds and methods can be used in combination with an antibiotic such as ciprofloxacin to treat or prevent conditions associated with bacterial infections, such as a *Bacillus anthracis* infection.

There has been relatively limited progress in identifying effective small molecule inhibitors of BoNTs with only a few exceptions. Disclosed herein is a series of rhodanine derivatives, which have been discovered to be potent and/or selective BoNT A inhibitors. Whereas previously reported rhodanine-based LF protease inhibitors were inactive against human metalloproteases MMP-2 and MMP-9 (5), several rhodanine derivatives of the invention can selectively inhibit MMP-2 and/or MMP-9.

The compounds disclosed herein can also be inhibitors of targets such as HCV NS3 protease (30), aldose reductase (31), β-lactamase (32), UDP-N-acetylmuramate/L-alanine ligase (33), cathepsin D (34), histidine decarboxylase, and Bcl-$x_L$ (35). The compounds can display a wide range of pharmacological activities, including antimicrobial (36-41), antiviral (42), anticonvulsant (42, 43), and antidiabetic (44, 45). For example, the compounds can be used for the treatment of the type II diabetes by contributing to improved glycemic control by increasing insulin sensitivity.

Accordingly, the rhodanine derivatives of the invention can be antitoxin protease inhibitors, such as anthrax LF inhibitors or BoNT/A inhibitors. The rhodanine derivatives of the invention were analyzed for potency and selectivity against LF and BoNT A as well as for solubility and in vitro ADME-Tox properties, cell-based assays and preliminary in vivo efficacy.

As used herein, the following terms and expressions have the indicated meanings. It will be appreciated that the methods of the present invention can employ and/or provide compounds that can contain asymmetrically substituted carbon atoms, and can be isolated in optically active or racemic forms. It is well known in the art how to prepare optically active forms, such as by resolution of racemic forms or by synthesis, from optically active starting materials.

All chiral, diastereomeric, racemic forms and all geometric isomeric forms of a structure are intended, unless the specific stereochemistry or isomeric form is specifically indicated. The processes to prepare or manufacture compounds useful in the present invention are contemplated to be practiced on at least a multigram scale, kilogram scale, multikilogram scale, or industrial scale. Multigram scale, as used herein, is preferably the scale wherein at least one starting material is present in 10 grams or more, more preferably at least 50 grams or more, even more preferably at least 100 grams or more. Multi-kilogram scale, as used herein, is intended to mean the scale wherein more than one kilogram of at least one starting material is used. Industrial scale as used herein is intended to mean a scale which is other than a laboratory scale and which is sufficient to supply product sufficient for either clinical tests or distribution to consumers.

One diastereomer of a compound disclosed herein may display superior activity compared with the other. When required, separation of the racemic material can be achieved by HPLC using a chiral column or by a resolution using a resolving agent such as camphonic chloride as in Tucker, et al., *J. Med. Chem.* 37:2437 (1994). A chiral compound described herein may also be directly synthesized using a chiral catalyst or a chiral ligand, e.g. Huffman, et al., *J. Org. Chem.* 60:1590 (1995).

The present invention is intended to include all isotopes of atoms occurring on the compounds useful in the present invention. Isotopes include those atoms having the same atomic number but different mass numbers. By way of general example and without limitation, isotopes of hydrogen include tritium and deuterium. Isotopes of carbon include C-13 ($^{13}C$) and C-14 ($^{14}C$).

General Definitions

As used herein, certain terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14th Edition, by R. J. Lewis, John Wiley & Sons, New York, N.Y., 2001.

The term "and/or" means any one of the items, any combination of the items, or all of the items with which this term is associated.

The singular forms "a," "an," and "the" include plural reference unless the context clearly dictates otherwise. Thus, for example, a reference to "a compound" includes a plurality of such compounds, so that a compound X includes a plurality of compounds X.

The term "about" can refer to a variation of ±5%, 10%, or 20% of the value specified. For example, "about 50" percent can in some embodiments carry a variation from 45 to 55 percent. For integer ranges, the term "about" can include one or two integers greater than and less than a recited integer.

It should be noted that references in the specification to "one embodiment", "an embodiment", "an example embodiment", etc., indicate that the embodiment described may include a particular feature, structure, or characteristic, but every embodiment may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

As used herein, "contacting" refers to the act of touching, making contact, or of bringing to immediate or close proximity, including at the molecular level, such as in vivo, in vitro, or in an aqueous solution.

Compound and Composition Definitions

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the compounds useful in the present invention can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., p. 1418 (1985), the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

"Stable compound" and "stable structure" are meant to indicate a compound that is sufficiently robust to survive isolation to a useful degree of purity from a reaction mixture, and formulation into an efficacious therapeutic agent. Only stable compounds are contemplated by the present invention.

The term "substituted" means that a specified group or moiety can bear one or more (e.g., 1, 2, 3, 4, 5, or 6) substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system. In cases where a specified moiety or group is not expressly noted as being optionally substituted or substituted with any specified substituent, it is understood that such a moiety or group is intended to be unsubstituted in some embodiments but can be substituted in other embodiments. The term substituted is intended to indicate that one or more hydrogens on the substituted atom or group is replaced with a selection from the indicated group(s), provided that the indicated atom's normal valency is not exceeded, and that the substitution results in a stable compound. Suitable substituent groups include, e.g., alkyl, alkenyl, alkynyl, alkoxy, halo, haloalkyl, hydroxy, hydroxyalkyl, aryl, aroyl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxyl amine, hydroxyl (alkyl)amine, and/or cyano.

The term "alkyl" refers to a monoradical branched or unbranched saturated hydrocarbon chain preferably having from 1 to 8 carbon atoms. This term is exemplified by groups such as methyl, ethyl, n-propyl, iso-propyl, n-butyl, iso-butyl, sec-butyl, n-hexyl, and the like.

The alkyl can optionally be substituted with one or more alkoxy, halo, haloalkyl, hydroxy, hydroxyalkyl, aryl, heteroaryl, heterocycle, cycloalkyl, alkanoyl, alkoxycarbonyl, amino, alkylamino, acylamino, nitro, trifluoromethyl, trifluoromethoxy, carboxy, carboxyalkyl, keto, thioxo, alkylthio, alkylsulfinyl, alkylsulfonyl, cyano, $NR_xR_x$ or $COOR_x$, wherein each $R_x$ is independently H or alkyl.

The alkyl can optionally be interrupted with one or more non-peroxide oxy (—O—), thio (—S—), sulfonyl (SO) or sulfoxide ($SO_2$).

The alkyl can optionally be at least partially unsaturated, thereby providing an alkenyl or alkynyl.

The term "alkoxy" refers to the groups alkyl-O—, where alkyl is defined herein. Preferred alkoxy groups include, e.g., methoxy, ethoxy, n-propoxy, iso-propoxy, n-butoxy, tert-butoxy, sec-butoxy, n-pentoxy, n-hexoxy, 1,2-dimethylbutoxy, and the like.

The alkoxy can optionally be substituted with one or more alkyl, halo, haloalkyl, hydroxy, hydroxyalkyl, aryl, heteroaryl, heterocycle, cycloalkyl, alkanoyl, alkoxycarbonyl, amino, alkylamino, acylamino, nitro, trifluoromethyl, trifluoromethoxy, carboxy, carboxyalkyl, keto, thioxo, alkylthio, alkylsulfinyl, alkylsulfonyl and cyano.

The term "aryl" refers to an unsaturated aromatic carbocyclic group of from 6 to 20 carbon atoms having a single ring (e.g., phenyl) or multiple condensed (fused) rings, wherein at least one ring is aromatic (e.g., naphthyl, dihydrophenanthrenyl, fluorenyl, or anthryl). Preferred aryls include phenyl, naphthyl and the like.

The aryl can optionally be substituted with one or more alkyl, alkoxy, halo, haloalkyl, hydroxy, hydroxyalkyl, heteroaryl, heterocycle, cycloalkyl, alkanoyl, alkoxycarbonyl, amino, alkylamino, acylamino, nitro, trifluoromethyl, trifluoromethoxy, carboxy, carboxyalkyl, keto, thioxo, alkylthio, alkylsulfinyl, alkylsulfonyl and cyano.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

The cycloalkyl can optionally be substituted with one or more alkyl, alkoxy, halo, haloalkyl, hydroxy, hydroxyalkyl, aryl, heteroaryl, heterocycle, alkanoyl, alkoxycarbonyl, amino, alkylamino, acylamino, nitro, trifluoromethyl, trifluoromethoxy, carboxy, carboxyalkyl, keto, thioxo, alkylthio, alkylsulfinyl, alkylsulfonyl and cyano.

The cycloalkyl can optionally be at least partially unsaturated, thereby providing a cycloalkenyl.

The term "halo" refers to fluoro, chloro, bromo, and iodo. Similarly, the term "halogen" refers to fluorine, chlorine, bromine, and iodine.

"Haloalkyl" refers to alkyl as defined herein substituted by 1-4 halo groups as defined herein, which may be the same or different. Representative haloalkyl groups include, by way of example, trifluoromethyl, 3-fluorododecyl, 12,12,12-trifluorododecyl, 2-bromooctyl, 3-bromo-6-chloroheptyl, and the like.

The term "heteroaryl" is defined herein as a monocyclic, bicyclic, or tricyclic ring system containing one, two, or three aromatic rings and containing at least one nitrogen, oxygen, or sulfur atom in an aromatic ring, and which can be unsubstituted or substituted, for example, with one or more, and in particular one to three, substituents, like halo, alkyl, hydroxy, hydroxyalkyl, alkoxy, alkoxyalkyl, haloalkyl, nitro, amino, alkylamino, acylamino, alkylthio, alkylsulfinyl, and alkylsulfonyl. Examples of heteroaryl groups include, but are not limited to, 2H-pyrrolyl, 3H-indolyl, 4H-quinolizinyl, 4nH-carbazolyl, acridinyl, benzo[b]thienyl, benzothiazolyl, β-carbolinyl, carbazolyl, chromenyl, cinnaolinyl, dibenzo[b,d] furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, naptho[2,3-b], oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrrolyl, quinazolinyl, quinolyl, quinoxalinyl, thiadiazolyl, thianthrenyl, thiazolyl, thienyl, triazolyl, and xanthenyl. In one embodiment the term "heteroaryl" denotes a monocyclic aromatic ring containing five or six ring atoms containing carbon and 1, 2, 3, or 4 heteroatoms independently selected from the group non-peroxide oxygen, sulfur, and N(Z) wherein Z is absent or is H, O, alkyl, phenyl or benzyl. In another embodiment heteroaryl denotes an ortho-fused bicyclic heterocycle of about eight to ten ring atoms derived therefrom, particularly a benz-derivative or one derived by fusing a propylene, or tetramethylene diradical thereto.

The heteroaryl can optionally be substituted with one or more alkyl, alkoxy, halo, haloalkyl, hydroxy, hydroxyalkyl, aryl, heterocycle, cycloalkyl, alkanoyl, alkoxycarbonyl, amino, alkylamino, acylamino, nitro, trifluoromethyl, trifluoromethoxy, carboxy, carboxyalkyl, keto, thioxo, alkylthio, alkylsulfinyl, alkylsulfonyl and cyano.

The term "heterocycle" refers to a saturated or partially unsaturated ring system, containing at least one heteroatom selected from the group oxygen, nitrogen, and sulfur, and optionally substituted with alkyl or C(=O)OR$^b$, wherein R$^b$ is hydrogen or alkyl. Typically heterocycle is a monocyclic, bicyclic, or tricyclic group containing one or more heteroatoms selected from the group oxygen, nitrogen, and sulfur. A heterocycle group also can contain an oxo group (=O) attached to the ring. Non-limiting examples of heterocycle groups include 1,3-dihydrobenzofuran, 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholine, piperazinyl, piperidine, piperidyl, pyrazolidine, pyrazolidinyl, pyrazolinyl, pyrrolidine, pyrroline, quinuclidine, and thiomorpholine.

The heterocycle can optionally be substituted with one or more alkyl, alkoxy, halo, haloalkyl, hydroxy, hydroxyalkyl, aryl, heteroaryl, cycloalkyl, alkanoyl, alkoxycarbonyl, amino, alkylamino, acylamino, nitro, trifluoromethyl, trifluoromethoxy, carboxy, carboxyalkyl, keto, thioxo, alkylthio, alkylsulfinyl, alkylsulfonyl and cyano.

Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles.

Another class of heterocyclics is known as "crown compounds" which refers to a specific class of heterocyclic compounds having one or more repeating units of the formula [—(CH$_2$—)$_a$A-] where a is equal to or greater than 2, and A at each separate occurrence can be O, N, S or P. Examples of crown compounds include, by way of example only, [—(CH$_2$)$_3$—NH—]$_3$, [—((CH$_2$)$_2$—O)$_4$—((CH$_2$)$_2$—NH)$_2$] and the like. Typically such crown compounds can have from 4 to 10 heteroatoms and 8 to 40 carbon atoms.

The term "alkanoyl" refers to C(=O)R, wherein R is an alkyl group as previously defined.

The term "acyloxy" refers to —O—C(=O)R, wherein R is an alkyl group as previously defined. Examples of acyloxy groups include, but are not limited to, acetoxy, propanoyloxy, butanoyloxy, and pentanoyloxy. Any alkyl group as defined above can be used to form an acyloxy group.

The term "alkoxycarbonyl" refers to C(=O)OR, wherein R is an alkyl group as previously defined.

The term "amino" refers to —NH$_2$, and the term "alkylamino" refers to —NR$_2$, wherein at least one R is alkyl and the second R is alkyl or hydrogen. The term "acylamino" refers to RC(=O)N, wherein R is alkyl or aryl.

As to any of the above groups, which contain one or more substituents, it is understood, of course, that such groups do not contain any substitution or substitution patterns which are sterically impractical and/or synthetically non-feasible. In addition, the compounds of this invention include all stereochemical isomers arising from the substitution of these compounds.

Selected substituents within the compounds described herein are present to a recursive degree. In this context, "recursive substituent" means that a substituent may recite another instance of itself. Because of the recursive nature of such substituents, theoretically, a large number may be present in any given claim. One of ordinary skill in the art of medicinal chemistry understands that the total number of such substituents is reasonably limited by the desired properties of the compound intended. Such properties include, by of example and not limitation, physical properties such as molecular weight, solubility or log P, application properties such as activity against the intended target, and practical properties such as ease of synthesis.

Recursive substituents are an intended aspect of the invention. One of ordinary skill in the art of medicinal and organic chemistry understands the versatility of such substituents. To the degree that recursive substituents are present in an claim of the invention, the total number will be determined as set forth above.

Obviously, numerous modifications and variations of the present invention are possible in light of the above teachings. It is therefore to be understood that within the scope of the appended claims, the invention may be practiced otherwise than as specifically described herein.

Certain compounds and methods of the invention include lethal factor inhibitor compound 1 (BI-11B1) and compound 2 (rosiglitazone), an inhibitor of peroxisome proliferators-activated receptor-gamma.

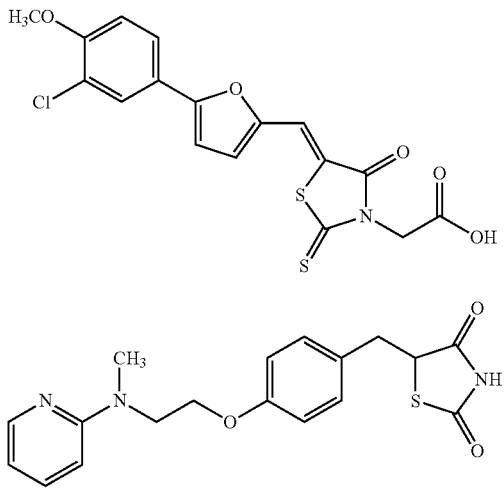

These compounds may be used in combination with the therapeutic compounds, compositions, and methods described herein.

Compounds of the Invention

The invention provides compounds of formula I wherein $R^1$ can be phenyl, substituted phenyl, heterocycle, or substituted heterocycle. Specific substituents include halo (e.g., F, Cl, Br, or I), trifluoromethyl, morpholinosulfonyl, phenylsulfonyl, alkoxy such as methoxy or ethoxy, benzyloxy, or halobenzyloxy.

Specific values for $R^2$ include —$(CH_2)CO_2H$, $C_2H_4SO_3H$, or -(1,1-dioxo-tetrahydro-thiophen-3-yl).

Specific values for $R^3$ include H, phenyl, or substituted phenyl. Specific substitutions for phenyl include 1-5 halo groups, each of which may be located at the 2, 3, 4, 5, and/or 6 position of the phenyl group. Similar positional substitutions can be made for other aryl, heteroaryl, or heterocyclic groups of other formulas of the invention.

In some embodiments, $R^1$ is not phenyl substituted with chloro. In other embodiments, $R^1$ is not phenyl substituted with halo. In yet other embodiments, $R^1$ is not phenyl substituted with halo, nitro, carboxy, or sulfonamide.

The invention provides compounds of formula II wherein $R^1$ can be H, halo, for example, chloro or bromo.

A specific values for $R^2$ is —$(CH_2)CO_2H$.

The bond represented by ---- can be absent or present. The alkene group of the thiazole ring of formula II can be attached to the bicyclic ring of formula II at a position either alpha or beta to $A^3$. Specific values for $A^{1-3}$ include CH, S, N, and/or NH.

The invention provides compounds of formula III wherein $R^1$ can be H, heterocycle, or heteroaryl. $R^1$ can also be linked to $R^{10}$ to form a group that includes an aryl, a heterocyclic, or a heteroaryl group, which can be optionally substituted, for example, with one or more halo or alkyl groups.

Specific values for $R^2$ include H or —$(CH_2)CO_2H$ and the bond represented by ---- can be absent or present.

Specific values for A include C, CH, and/or N. Specific values for Q are S or O.

Other specific values for the formulas described herein include the variables listed in Table A. Table A below illustrates various compounds of formulas I-VII and certain specific definitions of their corresponding variables. In some embodiments, the one or more groups from the variables of one formula can be included in the definition of one or more variables of another formula, and/or the one or more groups from the variables of one formula can be excluded from the definition of one or more variables of another formula.

TABLE A

Specific Compounds of the Invention.

| Compound No. | Chemical Name | Compound of Formula: | Substituent Values |
|---|---|---|---|
| 27 | (Z)-2-(4-oxo-2-thioxo-5-((3-(4-(trifluoromethyl)phenyl)-1H-pyrazol-4-yl)methylene)thiazolidin-3-yl)acetic acid | 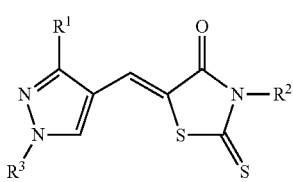 (I) | $R^1$ = 4-(trifluoromethyl)phenyl $R^2$ = $(CH_2)CO_2H$ $R^3$ = H |
| 29 | (Z)-2-(4-oxo-5-((1-phenyl-3-(thiophen-2-yl)-1H-pyrazol-4-yl)methylene)-2-thioxothiazolidin-3-yl)acetic acid | 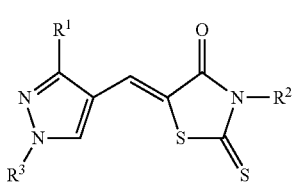 (I) | $R^1$ = -(thiophene-2-yl) $R^2$ = $(CH_2)CO_2H$ $R^3$ = Ph |

TABLE A-continued

Specific Compounds of the Invention.

| Compound No. | Chemical Name | Compound of Formula: | Substituent Values |
|---|---|---|---|
| 30 | (Z)-2-(5-((1,3-diphenyl-1H-pyrazol-4-yl)methylene)-4-oxo-2-thioxothiazolidin-3-yl)acetic acid | 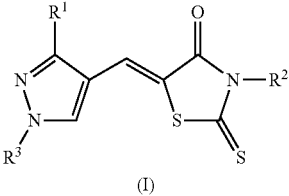 (I) | $R^1$ = Ph<br>$R^2$ = $(CH_2)CO_2H$<br>$R^3$ = Ph |
| 31 | (Z)-2-(5-((3-(4-(morpholinosulfonyl)phenyl)-1-phenyl-1H-pyrazo-4-yl)-methylene-4-oxo-2-thioxothiazolidin-3-yl)acetic acid | 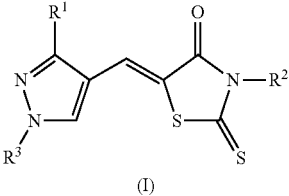 (I) | $R^1$ = 4-(morpholinosulfonyl)phenyl<br>$R^2$ = $(CH_2)CO_2H$<br>$R^3$ = Ph |
| 32 | (Z)-2-(5-((1-(2,4-difluorophenyl)-3-(pyridin-3-yl)-1H-pyrazol-4-yl)methylene)-4-oxo-2-thioxothiazolidin-3-yl)acetic acid | 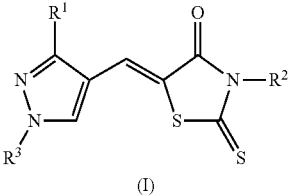 (I) | $R^1$ = N-pyridinium<br>$R^2$ = $(CH_2)CO_2H$<br>$R^3$ = (2,4-difluoro-phenyl) |
| 33 | (Z)-2-(5-((1,3-bis(4-fluorophenyl)-1H-pyrazol-4-yl)methylene)-4-oxo-2-thioxothiazolidin-3-yl)acetic acid | 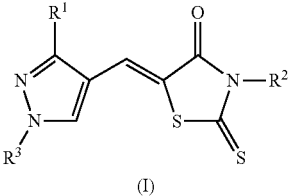 (I) | $R^1$ = 4-fluorophenyl<br>$R^2$ = $(CH_2)CO_2H$<br>$R^3$ = 4-fluorophenyl |
| 34 | (Z)-2-(5-((1,3-bis(4-chlorophenyl)-1H-pyrazol-4-yl)methylene)-4-oxo-2-thioxothiazolidin-3-yl)acetic acid | 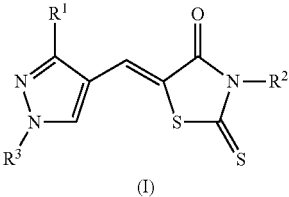 (I) | $R^1$ = (4-chlorophenyl)<br>$R^2$ = $(CH_2)CO_2H$<br>$R^3$ = (4-chlorophenyl) |
| 35 | (Z)-2-(5-((1,3-bis(4-bromophenyl)-1H-pyrazol-4-yl)methylene)-4-oxo-2-thioxothiazolidin-3-yl)acetic acid | 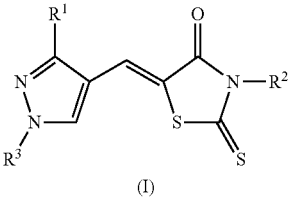 (I) | $R^1$ = (4-bromophenyl)<br>$R^2$ = $(CH_2)CO_2H$<br>$R^3$ = (4-bromophenyl) |
| 36 | (Z)-2-(5-((3-(4-methoxy-3-methylphenyl)-1-phenyl-1H-pyrazol-4-yl)methylene)-4-oxo-2-thioxothiazolidin-3-yl)acetic acid | 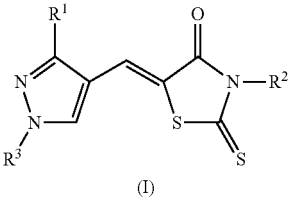 (I) | $R^1$ = (4-methoxy-3-methylphenyl)<br>$R^2$ = $(CH_2)CO_2H$<br>$R^3$ = Ph |

TABLE A-continued

Specific Compounds of the Invention.

| Compound No. | Chemical Name | Compound of Formula: | Substituent Values |
|---|---|---|---|
| 37 | (Z)-2-(5-((3-(4-ethoxy-2-methylphenyl)-1-phenyl-1H-pyrazol-4-yl)methylene)-4-oxo-2-thioxothiazolidin-3-yl)acetic acid | 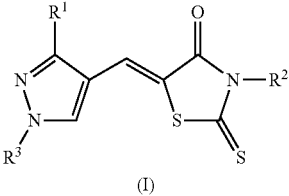 (I) | $R^1$ = (4-ethoxy-2-methylphenyl) <br> $R^2$ = $(CH_2)CO_2H$ <br> $R^3$ = Ph |
| 38 | (Z)-2-(5-((3-(4-(4-chlorobenzyloxy)phenyl)-1-phenyl-1H-pyrazol-4-yl)methylene)-4-oxo-2-thioxothiazolidin-3-yl)ethanesulfonic acid | 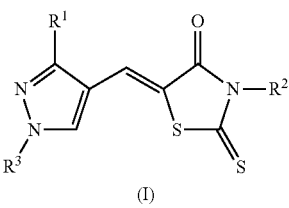 (I) | $R^1$ = (4-chlorobenzyloxy)phenyl <br> $R^2$ = $C_2H_4SO_3H$ <br> $R^3$ = Ph |
| 39 | (Z)-2-(5-((3-(2-methyl-2,3-dihydrobenzofuran-5-yl)-1-phenyl-1H-pyrazol-4-yl)methylene)-4-oxo-2-thioxothiazolidin-3-yl)ethanesulfonic acid | 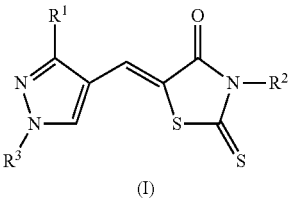 (I) | $R^1$ = (2-methyl-2,3-dihydrobenzofuran-5-yl) <br> $R^2$ = $C_2H_4SO_3H$ <br> $R^3$ = Ph |
| 40 | (Z)-2-(5-((3-(4-methoxyphenyl)-1-phenyl-1H-pyrazol-4-yl)methylene)-4-oxo-2-thioxothiazolidin-3-yl)ethanesulfonic acid | 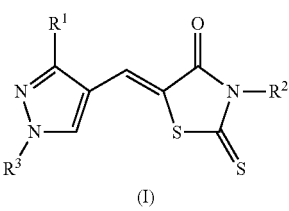 (I) | $R^1$ = (4-methoxyphenyl) <br> $R^2$ = $C_2H_4SO_3H$ <br> $R^3$ = Ph |
| 41 | (Z)-2-(5-((3-(4-chlorophenyl)-1-phenyl-1H-pyrazol-4-yl)methylene)-4-oxo-2-thioxothiazolidin-3-yl)ethanesulfonic acid | 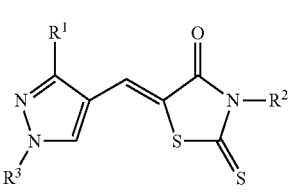 (I) | $R^1$ = (4-chlorophenyl) <br> $R^2$ = $C_2H_4SO_3H$ <br> $R^3$ = Ph |
| 42 | (Z)-2-(5-((3-(4-(morpholinosulfonyl)phenyl)-1-phenyl-1H-pyrazol-4-yl)methylene)-4-oxo-2-thioxothiazolidin-3-yl)ethanesulfonic acid | 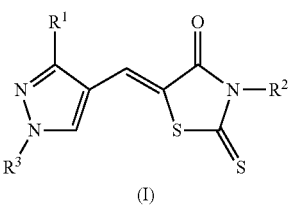 (I) | $R^1$ = (4-(morpholinosulfonyl)phenyl) <br> $R^2$ = $C_2H_4SO_3H$ <br> $R^3$ = Ph |
| 43 | (Z)-2-(4-oxo-5-((1-phenyl-3-(4-(piperidin-1-ylsulfonyl)phenyl)-1H-pyrazol-4-yl)methylene)-2-thioxothiazolidin-3-yl)ethanesulfonic acid | 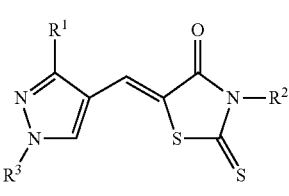 (I) | $R^1$ = 1-(phenylsulfonyl)piperidine <br> $R^2$ = $C_2H_4SO_3H$ <br> $R^3$ = Ph |

US 7,947,717 B2

TABLE A-continued

Specific Compounds of the Invention.

| Compound No. | Chemical Name | Compound of Formula: | Substituent Values |
|---|---|---|---|
| 44 | 3-(1,1-Dioxo-tetrahydro-thiophen-3-yl)-5-[1-(1,3-diphenyl-1H-pyrazol-4-yl)-meth-(Z)-ylidene]-2-thioxo-thiazolidin-4-one | 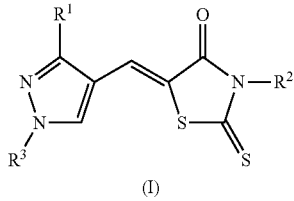 (I) | $R^1$ = Ph<br>$R^2$ = -(1,1-dioxo-tetrahydro-thiophen-3-yl)<br>$R^3$ = Ph |
| 45 | 5-[1-[3-(4-Chloro-phenyl)-1-phenyl-1H-pyrazol-4-yl]-meth-(Z)-ylidene]-3-(1,1-dioxo-tetrahydro-thiophen-3-yl)-2-thioxo-thiazolidin-4-one | 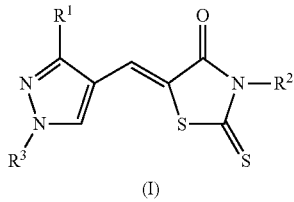 (I) | $R^1$ = 4-Chloro-phenyl<br>$R^2$ = -(1,1-dioxo-tetrahydro-thiophen-3-yl)<br>$R^3$ = Ph |
| 46 | (Z)-2-(5-((3-(4-ethoxy-3-fluorophenyl)-1-phenyl-1H-pyrazol-4-yl)methylene)-4-oxo-2-thioxothiazolidin-3-yl)acetic acid | 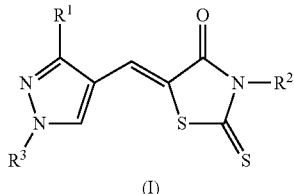 (I) | $R^1$ = 4-ethoxy-3-fluorophenyl<br>$R^2$ = (CH$_2$)CO$_2$H<br>$R^3$ = Ph |
| 57 | (Z)-2-(5-(benzo[b]thiophen-3-ylmethylene)-4-oxo-2-thioxothiazolidin-3-yl)acetic acid | 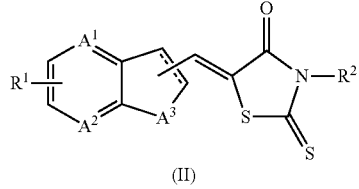 (II) | $R^1$ = H<br>$R^2$ = (CH$_2$)CO$_2$H<br>---- = Optional double bond present<br>$A^1$ = CH<br>$A^2$ = CH<br>$A^3$ = S |
| 58 | (Z)-2-(5-((5-bromobenzo[b]thiophen-3-yl)methylene)-4-oxo-2-thioxothiazolidin-3-yl)acetic acid | 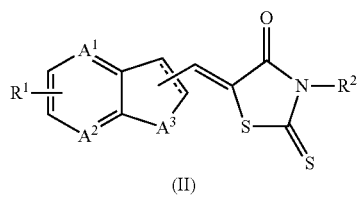 (II) | $R^1$ = Br<br>$R^2$ = (CH$_2$)CO$_2$H<br>---- = Optional double bond present<br>$A^1$ = CH<br>$A^2$ = CH<br>$A^3$ = S |
| 59 | (Z)-2-(5-((6,7-dihydrothieno[2,3-b]pyrazin-6-yl)methylene)-4-oxo-2-thioxothiazolidin-3-yl)acetic acid | 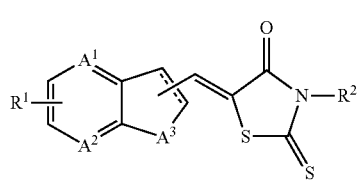 (II) | $R^1$ = H<br>$R^2$ = (CH$_2$)CO$_2$H<br>---- = Optional double bond present<br>$A^1$ = N<br>$A^2$ = N<br>$A^3$ = S |
| 60 | (Z)-2-(5-((1H-indol-3-yl)methylene)-4-oxo-2-thioxothiazolidin-3-yl)acetic acid | 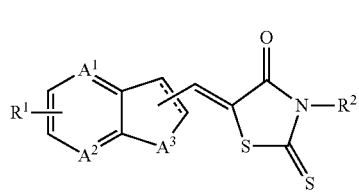 (II) | $R^1$ = H<br>$R^2$ = (CH$_2$)CO$_2$H<br>---- = Optional double bond present<br>$A^1$ = CH<br>$A^2$ = CH<br>$A^3$ = NH |

TABLE A-continued

Specific Compounds of the Invention.

| Compound No. | Chemical Name | Compound of Formula: | Substituent Values |
|---|---|---|---|
| 61 | (Z)-2-(5-((5-bromo-1H-indol-3-yl)methylene)-4-oxo-2-thioxothiazolidin-3-yl)acetic acid | 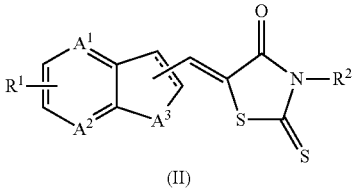 (II) | $R^1$ = Br<br>$R^2$ = $(CH_2)CO_2H$<br>---- = Optional double bond present<br>$A^1$ = CH<br>$A^2$ = CH<br>$A^3$ = NH |
| 2 | 5-(4-(2-(methyl(pyridin-2-yl)amino)ethoxy)benzyl)thiazolidine-2,4-dione | 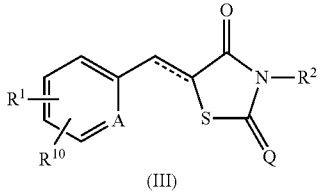 (III) | $R^1$ = 2-(methyl(pyridin-2-yl)amino)ethoxy<br>$R^{10}$, $R^2$ = H<br>---- = Optional double bond absent<br>A = CH<br>Q = O |
| 49 | (Z)-2-(5-(4-phenylbenzylidene)-4-oxo-2-thioxothiazolidin-3-yl)acetic acid | 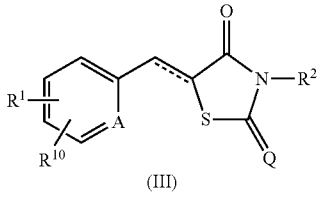 (III) | $R^1$ and $R^{10}$ together = 4-phenyl<br>$R^2$ = $(CH_2)CO_2H$<br>---- = Optional double bond Present<br>A = CH<br>Q = S |
| 50 | (Z)-2-(5-(3-(pyrrolidin-1-yl)benzylidene)-4-oxo-2-thioxothiazolidin-3-yl)acetic acid | 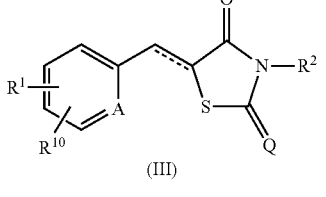 (III) | $R^1$ and $R^{10}$ together = N-pyrrolidino<br>$R^2$ = $(CH_2)CO_2H$<br>---- = Optional double bond Present<br>A = CH<br>Q = S |
| 51 | (Z)-2-(5-(4-(1,4-diazepan-1-yl)benzylidene)-4-oxo-2-thioxothiazolidin-3-yl)acetic acid | 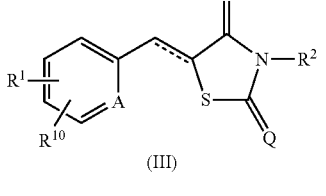 (III) | $R^1$ and $R^{10}$ together = (1,4-diazepan-1-yl)<br>$R^2$ = $(CH_2)CO_2H$<br>---- = Optional double bond Present<br>A = CH<br>Q = S |
| 52 | (Z)-2-(5-(3-(1H-pyrazol-1-yl)benzylidene)-4-oxo-2-thioxothiazolidin-3-yl)acetic acid | 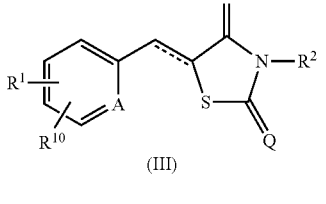 (III) | $R^1$ = N-pyrazolyl<br>$R^{10}$ = H<br>$R^2$ = $(CH_2)CO_2H$<br>---- = Optional double bond Present<br>A = CH<br>Q = S |
| 53 | (Z)-2-(5-(benzo[d][1,3]dioxol-5-ylmethylene)-4-oxo-2-thioxothiazolidin-3-yl)acetic acid | 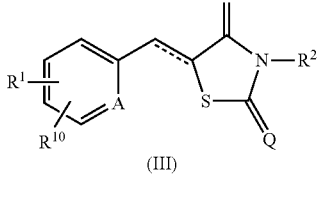 (III) | $R^1$ and $R^{10}$ together = (1,3-dioxole<br>$R^2$ = $(CH_2)CO_2H$<br>---- = Optional double bond Present<br>A = CH<br>Q = S |

TABLE A-continued

Specific Compounds of the Invention.

| Compound No. | Chemical Name | Compound of Formula: | Substituent Values |
|---|---|---|---|
| 54 | (Z)-2-(5-((2-methylquinolin-6-yl)methylene)-4-oxo-2-thioxothiazolidin-3-yl)acetic acid | (III) | $R^1$ and $R^{10}$ together = 2-methylpyridinium<br>$R^2$ = $(CH_2)CO_2H$<br>---- = Optional double bond Present<br>A = CH<br>Q = S |
| 55 | (Z)-2-(5-(dibenzofuran-6-ylmethylene)-4-oxo-2-thioxothiazolidin-3-yl)acetic acid | (III) | $R^1$ = benzofuran<br>$R^2$ = $(CH_2)CO_2H$<br>$R^{10}$ = H<br>$R^1$ = H<br>---- = Optional double bond Present<br>A = CH<br>Q = S |
| 56 | (Z)-2-(5-((6-bromopyridin-2-yl)methylene)-4-oxo-2-thioxothiazolidin-3-yl)acetic acid | (III) | $R^{10}$ = Br<br>$R^2$ = $(CH_2)CO_2H$<br>$R^1$ = H<br>---- = Optional double bonds Present<br>A = N<br>Q = S |
| 9 | (Z)-2-(5-((5-(3-nitrophenyl)furan-2-yl)methylene)-4-oxo-2-thioxothiazolidin-3-yl)ethanesulfonic acid | (IV) | $R^1$ = 3-nitrophenyl<br>$R^2$ = $(CH_2)_2SO_3H$<br>X = O<br>Y is =CH<br>Z is =CH |
| 10 | (Z)-2-(5-((5-(3-chlorophenyl)furan-2-yl)methylene)-4-oxo-2-thioxothiazolidin-3-yl)ethanesulfonic acid | (IV) | $R^1$ = 3-chlorophenyl<br>$R^2$ = $(CH_2)_2SO_3H$<br>X = O<br>Y is =CH<br>Z is =CH |
| 11 | (Z)-2-(5-((5-(3,4-dichlorophenyl)furan-2-yl)methylene)-4-oxo-2-thioxothiazolidin-3-yl)ethanesulfonic acid | (IV) | $R^1$ = 3,4-dichlorophenyl<br>$R^2$ = $(CH_2)_2SO_3H$<br>X = O<br>Y is =CH<br>Z is =CH |
| 12 | (Z)-2-(5-((5-(4-chlorophenyl)furan-2-yl)methylene)-4-oxo-2-thioxothiazolidin-3-yl)ethanesulfonic acid | (IV) | $R^1$ = 4-chlorophenyl<br>$R^2$ = $(CH_2)_2SO_3H$<br>X = O<br>Y is =CH<br>Z is =CH |

TABLE A-continued

Specific Compounds of the Invention.

| Compound No. | Chemical Name | Compound of Formula: | Substituent Values |
|---|---|---|---|
| 14 | (5Z)-5-{[5-(2,3-dichlorophenyl)-2-furyl]methylene}-3-(1,1-dioxidotetrahydrothien-3-yl)-2-thioxo-1,3-thiazolidin-4-one | (IV) | $R^1$ = (2,3-dichlorophenyl)<br>$R^2$ = -(1,1-dioxidotetrahydrothien-3-yl)<br>X = O<br>Y = CH<br>Z = CH |
| 15 | (5Z)-5-{[5-(2,3-dichlorophenyl)-2-furyl]methylene}-3-(1,1-dioxidotetrahydrothien-3-yl)-2-thioxo-1,3-thiazolidin-4-one | (IV) | $R^1$ = (2,3-dichlorophenyl)<br>$R^2$ = -(1,1-dioxidotetrahydrothien-3-yl)<br>X = O<br>Y = CH<br>Z = CH |
| 16 | (Z)-5-((5-(2,5-dichlorophenyl)furan-2-yl)methylene)-3-((tetrahydrofuran-2-yl)methyl)-2-thioxothiazolidin-4-one | (IV) | $R^1$ = 2,3-dichlorophenyl<br>$R^2$ = -(tetrahydrofuran-2-yl)methyl<br>X = O (Oxy)<br>Y is = CH<br>Z is = CH |
| 62 | (Z)-2-(5-(1-(2-(3-chlorophenylamino)-2-oxoethyl)-2-oxoindolin-3-ylidene)-4-oxo-2-thioxothiazolidin-3-yl)acetic acid | (V) | $R^1$ = Cl<br>n = 1<br>$R^2$ = $(CH_2)CO_2H$<br>$R^a$ = H |
| 63 | (Z)-2-(5-(1-(2-(m-toluidino)-2-oxoethyl)-2-oxoindolin-3-ylidene)-4-oxo-2-thioxothiazolidin-3-yl)acetic acid | (V) | $R^1$ = $CH_3$<br>n = 1<br>$R^2$ = $(CH_2)CO_2H$<br>$R^a$ = H |
| 47 | (Z)-2-(5-((7-bromo-2,3-dihydrothieno[3,4-b][1,4]dioxin-5-yl)methylene)4-oxo-2-thioxothiazolidin-3-yl)acetic acid | (VI) | $R^1$ = Br<br>$R^2$ = $(CH_2)CO_2H$<br>$R^{11}$ and $R^{12}$ together are 1,4-dioxane |

TABLE A-continued

Specific Compounds of the Invention.

| Compound No. | Chemical Name | Compound of Formula: | Substituent Values |
|---|---|---|---|
| 48 | (Z)-2-(5-((5-morpholinothiophen-2-yl)methylene)-4-oxo-2-thioxothiazolidin-3-yl)acetic acid | (VI) | $R^1$ = N-morpholino<br>$R^2$ = $(CH_2)CO_2H$<br>$R^{11}$ = H<br>$R^{12}$ = H |
| 66 | (Z)-2-(4-oxo-5-((5-(thiophen-2-yl)thiophen-2-yl)methylene)-2-thioxothiazolidin-3-yl)acetic acid | (VI) | $R^1$ = thiophene<br>$R^2$ = $(CH_2)CO_2H$<br>$R^{11}$ = H<br>$R^{12}$ = H |
| 67 | {(5Z)-5-[(5-{(Z)-[4-(carboxymethyl)-3-oxo-5-thioxodihydrothien-2(3H)-ylidene]methyl}thien-2-yl)methylene]-4-oxo-2-thioxo-1,3-thiazolidin-3-yl}acetic acid | (VI) | $R^1$ = (5-methylene-4-oxo-2-thioxo-tetrahydrothiophen-3-yl)acetic acid<br>$R^2$ = $(CH_2)CO_2H$<br>$R^{11}$ = H<br>$R^{12}$ = H |
| 18 | (Z)-2-(5-((2-(1-(tert-butoxycarbonyl)piperidin-4-yl)thiazol-4-yl)methylene)-4-oxo-2-thioxothiazolidin-3-yl)acetic acid | (VII) | $R^1$ = H<br>$R^2$ = $(CH_2)CO_2H$<br>X = N<br>Y = tert-butyl piperidine-1-carboxylate<br>Z = S |
| 20 | (Z)-2-(5-((5-(furan-2-yl)isoxazol-3-yl)methylene)-4-oxo-2-thioxothiazolidin-3-yl)acetic acid | (VII) | $R^1$ = H<br>$R^2$ = $(CH_2)CO_2H$<br>X = N<br>Y = O<br>Z = C-Furan |
| 19 | (Z)-2-(5-((2-methyl-4-phenylthiazol-5-yl)methylene)-4-oxo-2-thioxothiazolidin-3-yl)acetic acid | (VII) | $R^1$ = Ph<br>$R^2$ = $(CH_2)CO_2H$<br>X = S<br>Y = C—$CH_3$<br>Z = N |
| 17 | (Z)-2-(5-((2,5-dimethyloxazol-4-yl)methylene)-4-oxo-2-thioxothiazolidin-3-yl)acetic acid | (VII) | $R^1$ = $CH_3$<br>$R^2$ = $(CH_2)CO_2H$<br>X = N<br>Y = C—$CH_3$<br>Z = O |

Preparation of Compounds of the Invention

The compounds of the invention can be prepared using various standard techniques known to those skilled in the art or by the methods described in the Examples below. Many known compounds are commercially available from a chemical supplier, such as Maybridge, Chembridge and Chemnavigator (San Diego, Calif.).

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Pharmaceutical Compositions

The compounds of formulas I-VII can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I-VII to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of the formulas described herein can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of the formulas described herein in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 mg to 1000 mg, conveniently 10 mg to 750 mg, most conveniently, 50 mg to 500 mg of active ingredient per unit dosage form.

Ideally, the active ingredient should be administered to achieve peak plasma concentrations of the active compound of from about 0.5 to about 75 µM, preferably, about 1 to 50 µM, most preferably, about 2 to about 30 µM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The ability of a compound of the invention to inhibit LF protease activity may be determined using pharmacological models which are well known to the art, or using the procedures described in the Examples below.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1

Compounds of the Invention as Selective Protease Inhibitors

Methods And Materials

Compounds and reagents. Compounds 2-16, 29, 31, 36-46, 53, 60, 62, and 63 were purchased from Sigma Aldrich (St. Louis, Mo., USA). Compound 68 was purchased from Astatech, Inc (Bristol, Pa., USA). All common chemicals, reagents, and buffers were purchased from Sigma-Aldrich or Acros (Geel, Belgium). Synthetic details of the rhodanine derivatives 17-28, 30, 32-35, 47-52, 54-59, and 61 are described in Example 3. Compounds 1 and 64-67 were synthesized and characterized within our laboratory as described previously (*Proc. Natl. Acad. Sci. U.S.A.;* 102:9499-9504, *J. Med. Chem.;* 49:27-30). Characterization of each rhodanine derivative was obtained by means of NMR spectroscopy, mass spectrometry, and/or elemental analysis as reported in Example 3. Recombinant LF, MAPKKide®, BoNT A, and SNAPtide® were purchased from List Biological Laboratories (Campbell, Ca., USA). The MMP-2 and MMP-9 assay kits were purchased from Anaspec, Inc. (San Jose, Ca., USA).

MAPKKide® assay. The fluorescence peptide cleavage assay (100 µL) was performed in a 96-well plate in which each reaction mixture contained MAPKKide® (4 µM) and LF (50 nM) (List Biological Laboratories) in 20 mM HEPES, pH 7.4, and the screening compounds. Kinetics of the peptide cleavage was examined for 30 min by using a fluorescence plate reader (Victor™²V, Perkin Elmer, Waltham, Mass., USA) at excitation and emission wavelengths of 485 and 535 nm, respectively, and $IC_{50}$ values were obtained by dose-response measurements. For selected compounds, Lineweaver-Burk analysis was also carried out to verify that the compounds are competitive against the substrate. The $K_m$ and $V_{max}$ values of the MAPKKide® cleavage by LF were determined at 25° C. by using the same experimental condition described above for the fluorescence screening assay but with increasing MAPKKide® concentrations (10, 8, 4, 2, and 1 µM). The $K_i$ and $K_{m(app)}$ were calculated at 5 and or 10 µM inhibitor concentration.

SNAPtide® assay. The fluorescence peptide cleavage assay (50 µL) was performed in a 96-well plates in which each reaction mixture contained SNAPtide® (30 µM) and BoNT A (20 nM) (List Biological Laboratories) in 20 mM HEPES, 0.3 mM $ZnCl_2$, 1.25 mM DTT, 0.1% Tween-20, pH 8.0, and the screening compounds. Kinetics of the peptide cleavage was examined for 30 min by using a fluorescence plate reader (Victor™²V, Perkin Elmer) at excitation and emission wavelengths of 485 and 535 nm, respectively, and $IC_{50}$ values were obtained by dose-response measurements. The $K_m$ and $V_{max}$ values of the SNAPtide® cleavage by BoTN A were determined at 25° C. by using the same experimental condition described above for the fluorescence screening assay, but with increasing SNAPtide® concentrations (100, 60, 30, 10, and 1 µM).

MMP-2 and MMP-9 assay. This assay was performed as outlined in the Anaspec MMP assay kit (Cat. No. 71151/71155). The fluorescence peptide cleavage assay (50 µL) was performed in a 96-well plate in which each reaction mixture contained 5-FAM/QXLTM520 (60 µL; diluted 1:100 in assay buffer) and MMP-2 or MMP-9 (10 µg/mL; pro-MMP-2 and pro-MMP-9 are first activated with 1 mM APMA for 20 min or 2 h, respectively) in Enzolyte™ 520 MMP-2 assay buffer, and the screening compounds (compound 1-6; each compound at 20 µM). Kinetics of the peptide cleavage was examined every 5 min for 30 min by using a fluorescence plate reader (Victor™²V, Perkin Elmer) at excitation and emission wavelengths of 485 and 535 nm, respectively, and percent inhibition values were obtained.

ADME-TOX Studies. In vitro Evaluation of Chemical Stability of selected LF inhibitors in PBS for 24 hours (*J. Biomolecular Screening;* 8: 292-304; *J. Biomolecular Screening;* 11: 40-7). Chemical stability was evaluated in PBS (1.9 mM $NaH_2PO_4$, 8.1 mM $Na_2BPO_4$, 150 mM NaCl, pH 7.4). An accurately weighted amount of analyzed compounds was dissolved in DMSO (10 mM stock), and then reconstituted in PBS at a 100 uM concentration following HPLC-UV analysis ("zero" point). Samples in PBS were incubated in closed vials at 37° C. for 24 h in the dark following HPLC-UV analysis ("24-hours" point). Observed UV peak area ratio of each tested compound versus internal standard (IS) was calculated. The percentages of the remaining parent compounds was defined as the ratio of the parent compounds peak area at "zero" point to the peak area at "24 hours" point multiplied by 100%.

Determination of aqueous solubility by nephelometric assay (*Anal. Chem.;* 72: 1781-7). The purpose of this study was to measure the aqueous solubility of selected LF inhibitors determined by using nephelometry-based method described in the literature. Compounds were dissolved to 10 mM in 100% DMSO. Solubility of compounds was measured in PBS (pH 7.4), 5% DMSO at Room Temperature (around 23° C.). Aqueous solubility of acetylsalicylic acid was determined to validate the assay. It was found to be >100 µg/ml at the day of experiment, which corresponds to the reported literature value of at least 2.17 mg/mL (*The Merck index*, $10^{th}$ ed), 2.7 mg/mL (Sigma Aldrich Catalog, 2004-2005).

Determination of cytotoxicity (*J. Immunol. Meth.;* 213: 157-67). The method is based on the measurement of the metabolic activity of living cells using the resazurin system. The key component is the oxidoreduction indicator dye resazurin. Bioreduction of the dye by viable cells reduces the amount of its oxidized form [blue] and concomitantly increases the amount of its fluorescent intermediate (*Pharmacol. Rep.;* 58: 453-72), indicating the degree of cytotoxicity caused by the test material.

In the day of the experiment cells HepG2 ($5*10^5$ cells/ml) in medium DMEM with 10% FBS (HyClone Standard) were seeded into all wells of 96-well plates with the exception of wells E1-H1 where is medium DMEM with 10% FBS without cells. Controls: in wells A1-H1-5 µl 10% DMSO. In all other wells except of controls 5 µl tested compounds solutions in 10% DMSO were added following by 72 hours incubation at 37° C. in a humidified 5% $CO_2$ incubator. In each well 10 µl AlamarBlue were added. The plate were incubated 2 hours at 37° C. in a humidified 5% $CO_2$ incubator and the fluorescence of the AlamarBlue was measured on SAFIRE, Tecan with excitation at 570 nm and emission 595 nm.

Determination of permeability by Parallel Artificial Membrane Permeation Assay (*J. Med. Chem.;* 44: 923-30; *J. Med. Chem.;* 41: 1007-10). The permeability was determined by using PAMPA method described in the literature. The selected inhibitors were dissolved in DMSO to 10 mM. The tested compounds and controls were diluted with PBS to 1.67 mM and mixed well by pipetting, centrifuged for 5 min at 3500 rpm, followed by the addition of 280 µl of PBS, 5% DMSO to acceptor plate. Then add 5 µl of 2% L-α-Phosphatidylcholine suspension in dodecane to the membrane of the donor plate. immediately add 98 µl of PBS to donor plate and make the sandwich with the acceptor plate. Add 42 µl of tested compounds and controls dilutions to the acceptor plate. Cover the plate, place into camera and incubate for 16 hours. Make the equilibrium plate, add 225 µl of PBS, 3.7% DMSO and 25 µl of tested compounds and controls dilutions to UV plate. After 16 hours pull the donor plate out and transfer 250 µl from acceptor plate to UV plate. Scan UV plate on Safire (Tecan) plate reader from 245 to 450 nM with step 5 nM. Permeabilities of 4 reference compounds were determined to validate the assay. It was found to be: Lucifer Yellow—Low, Furosemid—Low, Metoprolol—High, Propranolol—High; at the day of experiment, which corresponds to the reported literature data.

Interaction studies of selected LF inhibitors with human MDR1 ABCB1/Pgp (Pgp Calcein Transport Assay) (*Blood*, 91: 4480-8; *Antimicrob Agents Chemother.*, 42: 3157-62; *FEBS Lett.*, 383: 99-104). The objective of this study was to evaluate the selected LF inhibitors to observe inhibition of P-glycoprotein mediated transport of calcein-AM out of the cell. Potency of the compounds was determined by the dose response experiment where the compounds were tested at 8 concentrations in triplicate.

Cell culture: Cell line was maintained in RPMI 1640 supplemented with 10% fetal bovine serum (HyClone, Standard), 100 units/ml of penicillin, 100 mg/ml of streptomycin, 2 mM glutamine, and 10 nM vincristine.

Calcein AM efflux assay: For the calcein-AM efflux assay, K562/i-S9 cells were seeded on 96-well (Costar) tissue culture plates at cell density of $5×10^6$ cells/well. Cells were cultured in 100 µl of serum free RPMI 1640 without vincristine. Controls: in wells A1-D1: 5 µl 1 mM verapamil solution; in wells E1-H1: 5 µl 20% DMSO in PBS.

Assay Protocol: 5 µl of tested compound solutions in 20% DMSO were added to corresponding wells followed by 15 minutes incubation at 37° C. Then 5 µl of 2 µM calcein-AM solution was added to each well. The plates were incubated at 37° C. for 2 hours. Then the plates were centrifuged, the supernatant was removed and the cells were resuspended in 100 µl of cold PBS (pH 7.4). The fluorescence was measured using Safire (Tecan) plate reader at 490/516 nm excitation/emission. Verapamil $IC_{50}$ was determined to validate the assay. On the day of the experiment, verapamil $IC_{50}$ was equal to 4.69 µM, which corresponds to the reported literature value of 2-5 µM. The rate of calcein accumulation in the absence or presence of compounds was calculated in Prism software (GraphPad). Fluorescent background was subtracted from the RFU data points.

Interaction studies of selected LF inhibitors with human CYP 2C19 (*Anal. Biochem.*, 248: 188-90; *Biopharm. Drug Dispos.*, 24: 375-84; *Drug Metab. Dispos.*, 29: 1196-200; *Drug Metab. Dispos.*, 28: 1440-8). The objective of this study was to evaluate the ability of the selected LF inhibitors to inhibit CYP 2C19 mediated transformation of 3-cyano-7-ethoxycoumarin (CEC).

Dilute compound stock solution (10 mM) to 5 mM by 100% DMSO. Dilute this solution by water up to 500 µM just before use. Rows A-G are serial dilutions (3-fold) of the test compound (DMSO concentration is 10%.). Add 35 µl reaction buffer (final concentrations: 50 mM $K_xPO_4$, pH 7.4, 1.3 mM $NADP^+$, 3.3 mM G6P, 3.3 mM $MgCl_2$, 0.4 U/ml GPD, 0.4 mg/ml BSA, 25 µM CEC) to every well. Add 5 µl diluted tested compounds to respective wells. Add 5 µl Tranylcypromine to the Control⁺ wells. Add 5 µl 10% DMSO to the Control wells. Read fluorescence (Safire, $E_x$=420 nm, $E_m$=460 nm, bandwidth 5 nm, Gain-150, Z-position 5300 µm) (optional). Add 10 µl CYP 2C19 solution (10 pmol/ml) to every well except for blank (add 10 µl PBS into blank wells). Incubate for 60 minutes at 37° C. Read fluorescence at once (Safire, $E_x$=420 nm, $E_m$=460 nm, bandwidth 5 nm, Gain-150, Z-position 5300 μm). The $IC_{50}$ values were calculated using GraphPad Prism V. 3.03. Inhibition constant ($IC_{50}$) of tranylcypromine was determined to validate the assay. It was found to be 0.69 μM, which corresponds to the reported literature data. Interaction studies of selected inhibitors with human CYP1A2, CYP2C9, CYP2D6, CYP3A4 were conducted similar to the procedure above.

In Vitro Metabolic Stability Assay with Rat Hepatocytes. (3, 4, 8)

1. Prepare a suspension of hepatocytes:
   a) Hepatocyte preconditioning: place 10 mL of the Hepatocyte Incubation Media to the vial with rat hepatocytes (1.5 ml) and shake for 5 minutes in centrifuge tube; centrifuge for 2 minutes at 1,000×g; remove supernatant (9 ml);
   b) add 3 mL Hepatocyte Incubation Media and shake for 2-3 minutes;
   c) 10 ul of cell suspension stained with methylene blue and subjected to Goryayev chamber to count the percentage of living cells (translucent);
   d) reconstitute hepatocytes in PBS, pH 7.4 to final concentration of $1 \cdot 10^6$/mL;
2. Prepare incubation mixtures (in triplicates):
   a) place the final hepatocyes mixture of 180 uL in 96-well cluster tubes;
   b) add tested compound (20 uL of 500 uM stock solution) to hepatocyte mixture;
   c) place in $CO_2$-incubator at 37° C. for 60 and 120 minutes;
   d) at the end of each incubation period (0, 60 and 120 min at 37° C.) 200 ul of acetonitrile was added to stop reaction, the tubes were vortex-mixed for 15 min to precipitate proteins;
3. Centrifuge the samples for 15 minutes at 6000×g.
4. The supernatant was immediately analyzed by HPLC-UV-DAD.

In vitro Plasma Stability Assay (*Eur. J Pharm. Sci.*, 22: 25-31). Compound stability was tested in rat plasma. The incubation mixture contained 180 uL of plasma and 20 uL of 500 uM drug stock solution in PBS (1.9 mM $NaH_2PO_4$, 8.1 mM $Na_2HPO_4$, 150 mM NaCl, pH 7.4). At the end of each incubation period (0, 30 minutes at 37° C.) 200 uL of ice-cold acetonitrile 1/1 (v/v) was added, the tubes were vortex-mixed for 20 s to precipitate proteins, left on ice for 30 min and centrifuged for 5 min at 15,000×g. The supernatant was immediately analyzed by HPLC-UV-DAD. Diclofenac was used as a positive control.

In Vitro Human/Rat Liver S9 Stability Assay (*Chem. Biol. Interact.*, 121: 17-35; *Drug Discov. Today*, 6: 357-66). Incubation solutions were prepared containing microsomal protein in phosphate buffer (1 mg/mL) and a NADP-regenerating system:

| Reagents | Per well Volume (μL) | Final conc. |
|---|---|---|
| buffer | 60 | |
| Test compound | 10 | 50 μM |
| protein | 10 | 1 mg/ml |
| NADPH | 20 | 2 mM |
| Volume of incubation | 100 | |

The reaction was initiated by addition of a test compound after preincubation at 37° C. for 2-3 minutes. At the end of each incubation period (0, 30 and 60 min at 37° C.) 100 μl of acetonitrile was added to stop reaction, the tubes were vortex-mixed for 20 sec to precipitate proteins, kept on ice and centrifuged for 15 min at 6,150×g. The corresponding loss of parent compound was determined by HPLC-UV. Diclofenac (50 uM) was used as a positive control.

Determination of HERG inhibition by radioligand assay (*Eur. J. Pharmacol.*, 430: 147-8; *Biophys. J.*, 74: 230-41). Tested compounds were diluted by DMSO to 1.2 mM. 5 μl of 1.2 mM compounds solutions or controls in DMSO were added to the wells according to the assay plate layout. 95 μl of assay buffer was added, 50 μl of 5.8 nM Astemizole, [O-Methyl-$_3$H] (7 nCi/well) in assay buffer was added, 50 μl of membrane suspension in assay buffer was added. The assay plate was incubated for 1 h at rt with shaking (300 rpm). The membranes were then harvested on glass fibre filter. The filter was dried and sealed with melt-on scintillator. The radioactivity was counted on a PerkinElmer Microbeta® Jet.

Cell-based assay. Murine macrophage-like RAW 264.7 cells are grown to confluence in wells of a 48-well plate in DMEM supplemented with 10% fetal calf serum. The cells are then replenished with fresh medium (0.1 mL per well) and next incubated with the increasing concentrations of inhibitors (0.1-50 μM) for 4 h. A known hydroxamate inhibitor of the LF metalloproteinase activity, GM6001 ($K_i \approx 5$ μM; 46) is included in the assay as a control. Anthrax protective antigen-83 (PA83) and LF are then added to the final concentration of 500 ng mL and 25 ng mL, respectively. After incubation for an additional 1 h, cell viability is assessed by 3,[4,5-dimethylthiazol-2-yl]-2,5-diphenyltetrazolium bromide (MTT) staining. Cells are incubated with 0.5 mg/mL MTT in DMEM for 45 min at 37° C.; the medium is aspirated, and the blue pigment produced by the viable cells is solubilized with 0.5% SDS/25 mM HCl in 90% isopropyl alcohol. The concentration of oxidized MTT in the samples is measured at 570 nm. Each datum point represents the results of at least three independent experiments performed in duplicate. The percentage of viable cells is calculated by using the following equation:

$$[(A_{570} \text{ of cells treated with } LF, PA83, \text{ and inhibitor}) - (A_{570} \text{ of cells treated with } LF \text{ and } PA83)]/[(A_{570} \text{ of cells treated with } LF \text{ alone}) - (A_{570} \text{ of cells treated with } LF \text{ and } PA83)].$$

Animal experiments with anthrax spores. Purification of anthrax spores and the inhalation model of anthrax using A/J mice was described previously (47-49). A/J mice (eight mice per group) received *B. anthracis* Sterne spores (4 H $10^5$/animal in 20 μL of DMSO). On the day following infection, mice received the LF inhibitor compound 34 (25 mg/kg intraperitoneal) in DMSO and then continued to receive injections once daily for the remainder of the experiment. Control mice received an equal volume of DMSO. Mice treated with cipro received 25 mg/kg subcutaneous treatments daily beginning on the fourth day following infection.

Molecular modeling. Docking studies were performed with GOLD (Version 2.1, The Cambridge Crystallographic Data Centre, Cambridge, UK) (50-52) and analyzed with Sybyl® software (Tripos, St Louis, Mo., USA). Molecular surfaces were generated with MOLCAD (53). The X-ray co-ordinates of BoNT A (PDB-ID 2G7N; 54) and LF (PDB-ID 1YQY; 55) were used to dock the compounds. Molecular models were generated with CONCORD (56) and energy minimized with Sybyl. For each compound, 10 solutions were generated and subsequently ranked according to Chemscore (52). Top solutions were used to represent the docked geometry of the compounds reported in FIG. 2.

Discussion

The $IC_{50}$ and $K_i$ values against LF were obtained using the same procedure as described previously (5, 6, 57) and tested selected inhibitors against BoNT A and MMP-2/-9 (57). Several of the rhodanine compounds of the invention illustrated in Tables 1-7 were synthesized as described in Example 3 and together with additional commercially available derivatives formed six subclasses. The first subclass included an aromatic moiety attached to a furan ring as shown in Table 1.

TABLE 1

Furan rhodanine derivatives and IC$_{50}$ values against lethal factor (LF), BoTN/A.

| Compd. | Ar | R | LF IC$_{50}$ (μM) | BoNT/A IC$_{50}$ (μM) |
|---|---|---|---|---|
| 3 | 3-O$_2$N-C$_6$H$_4$- | —CH$_2$CO$_2$H | 3.45 | >200 |
| 4 | 4-O$_2$N-2-Cl-C$_6$H$_3$- | —CH$_2$CO$_2$H | 2.10 | 11.8 |
| 5 | 4-Br-C$_6$H$_4$- | —CH(CO$_2$H)CH$_2$CO$_2$H | 3.98 | 51.6 |
| 6 | 4-O$_2$N-C$_6$H$_4$- | —CH(CO$_2$H)CH$_2$CH$_2$CO$_2$H | 4.91 | 148 |
| 7 | 3-O$_2$N-C$_6$H$_4$- | —CH(Ph)CO$_2$H | 2.18 | >200 |
| 8 | 3-Cl-C$_6$H$_4$- | —CH(Ph)CO$_2$H | 4.34 | 127 |
| 9* | 3-O$_2$N-C$_6$H$_4$- | —(CH$_2$)$_2$SO$_3$H | 1.09 | 9.72 |
| 10 | 3-Cl-C$_6$H$_4$- | —(CH$_2$)$_2$SO$_3$H | 1.70 | 19.9 |
| 11 | 3,4-Cl$_2$-C$_6$H$_3$- | —(CH$_2$)$_2$SO$_3$H | 1.78 | 11.1 |
| 12 | 4-Cl-C$_6$H$_4$- | —(CH$_2$)$_2$SO$_3$H | >200 | >200 |

TABLE 1-continued

Furan rhodanine derivatives and IC$_{50}$ values against lethal factor (LF), BoTN/A.

| Compd. | Ar | R | LF IC$_{50}$ (μM) | BoNT/A IC$_{50}$ (μM) |
|---|---|---|---|---|
| 13 | 2,4-dichlorophenyl | —CH(Ph)CO$_2$H | 1.20 | >200 |
| 14 | 2,3-dichlorophenyl | methyl-sulfolane | >100 | >200 |
| 15 | 2,4-dichlorophenyl | methyl-sulfolane | >50 | >100 |
| 16 | 2,4-dichlorophenyl | ethyl-tetrahydrofuran | >25 | >50 |

Compounds did not inhibit MMP-2 and MMP-9 appreciably up to 50 μM with the exception of compound 9 (MMP-2-IC$_{50}$ = 16.3 μM).

These data further confirmed the importance of an acid moiety, whether it is a carboxylic or sulfonic acid, as the absence of this group resulted in compounds with markedly reduced activity. The compounds of Table 1 were less effective in targeting BoNT/A, and also generally did not appreciably inhibit MMP-2 and MMP-9.

In further subclasses the rhodanine acetic acid and/or sulfonic acid moieties were fixed, but the furan ring was replaced with an oxazole/thiazole (Table 2), isoxazole (Table 3), or a pyrazole (Table 4).

TABLE 2

Oxazole/thiazole rhodanine derivatives and IC$_{50}$ values against lethal factor (LF), BoTN/A, MMP-2, and MMP-9.

| Compd. | Ar | LF IC$_{50}$ (μM) | BoNT/A IC$_{50}$ (μM) | MMP2 IC$_{50}$ (μM) | MMP9 IC$_{50}$ (μM) |
|---|---|---|---|---|---|
| 17 | 2,5-dimethyl-4-methyl-oxazole | 100 | >200 | >100 | >100 |

TABLE 2-continued

Oxazole/thiazole rhodanine derivatives and IC$_{50}$ values against lethal factor (LF), BoTN/A, MMP-2, and MMP-9.

| Compd. | Ar | LF IC$_{50}$ (μM) | BoNT/A IC$_{50}$ (μM) | MMP2 IC$_{50}$ (μM) | MMP9 IC$_{50}$ (μM) |
|---|---|---|---|---|---|
| 18 | BocN-piperidinyl-(4-methylthiazol-2-yl) | 20 | 176 | >100 | >100 |
| 19 | 2-methyl-4-phenyl-5-methylthiazolyl | 41.0 | >200 | >100 | >100 |

TABLE 3

Isoxazole rhodanine derivatives and IC$_{50}$ values against lethal factor (LF), BoTN/A, MMP-2, and MMP-9.

| Compd. | Ar | LF IC$_{50}$ (μM) | BoNT/A IC$_{50}$ (μM) | MMP2 IC$_{50}$ (μM) | MMP9 IC$_{50}$ (μM) |
|---|---|---|---|---|---|
| 20 | 2-furyl | 17 | >200 | 39.4 | >100 |
| 21 | phenyl | 18.7 | >200 | >100 | 50.0 |
| 22 | 4-methylphenyl | 5.9 | 130 | <10 | >100 |
| 23 | 4-methoxyphenyl | 7.8 | 194 | 6.62 | >100 |
| 24 | 4-chlorophenyl | 5.2 | 82.7 | 19.2 | >100 |

TABLE 3-continued

Isoxazole rhodanine derivatives and IC$_{50}$ values against lethal factor (LF), BoTN/A, MMP-2, and MMP-9.

| Compd. | Ar | LF IC$_{50}$ (μM) | BoNT/A IC$_{50}$ (μM) | MMP2 IC$_{50}$ (μM) | MMP9 IC$_{50}$ (μM) |
| --- | --- | --- | --- | --- | --- |
| 25 | 4-F-C$_6$H$_4$- | 12.4 | >200 | 10.0 | >100 |
| 26 | 4-Br-C$_6$H$_4$- | 17.3 | >200 | >100 | 27.4 |

TABLE 4

Pyrazole rhodanine derivatives and IC$_{50}$ values against lethal factor (LF), BoTN/A.

| Compd. | Ar | R | LF IC$_{50}$ (μM) | BoNT/A IC$_{50}$ (μM) |
| --- | --- | --- | --- | --- |
| 27 | 4-CF$_3$-phenyl-(4-methyl-1H-pyrazol-3-yl) | —CH$_2$CO$_2$H | 24.6 | >200 |
| 28 | 4-Cl-phenyl-(3-methyl-1H-pyrazol-5-yl) | —CH$_2$CO$_2$H | >100 | >200 |
| 29 | 1-Ph-4-methyl-3-(thiophen-2-yl)-pyrazole | —CH$_2$CO$_2$H | 3.07 | 160 |
| 30 | 1-Ph-3-Ph-4-methyl-pyrazole | —CH$_2$CO$_2$H | 6.25 | 111 |
| 31 | 1-Ph-4-methyl-3-[4-(morpholinosulfonyl)phenyl]-pyrazole | —CH$_2$CO$_2$H | 4.26 | >200 |

TABLE 4-continued

Pyrazole rhodanine derivatives and IC$_{50}$ values against lethal factor (LF), BoTN/A.

| Compd. | Ar | R | LF IC$_{50}$ (μM) | BoNT/A IC$_{50}$ (μM) |
|---|---|---|---|---|
| 32* | 2,4-difluorophenyl-pyrazole-pyridinyl | —CH$_2$CO$_2$H | 2.99 | 71.5 |
| 33* | bis(4-fluorophenyl)-pyrazole | —CH$_2$CO$_2$H | 4.22 | 52.6 |
| 34 | bis(4-chlorophenyl)-pyrazole | —CH$_2$CO$_2$H | 2.95 | 8.18 |
| 35 | bis(4-bromophenyl)-pyrazole | —CH$_2$CO$_2$H | 3.35 | 5.45 |
| 36 | Ph-pyrazole-(3-methyl-4-methoxyphenyl) | —CH$_2$CO$_2$H | 3.58 | 127 |
| 37 | Ph-pyrazole-(2-methyl-4-ethoxyphenyl) | —CH$_2$CO$_2$H | 4.87 | 130 |
| 38* | Ph-pyrazole-phenyl-O-CH$_2$-(4-chlorophenyl) | —C$_2$H$_4$SO$_3$H | 2.45 | >200 |
| 39 | Ph-pyrazole-(2-methyl-2,3-dihydrobenzofuran) | —C$_2$H$_4$SO$_3$H | 2.29 | >200 |

TABLE 4-continued

Pyrazole rhodanine derivatives and IC$_{50}$ values against lethal factor (LF), BoTN/A.

| Compd. | Ar | R | LF IC$_{50}$ (μM) | BoNT/A IC$_{50}$ (μM) |
|---|---|---|---|---|
| 40* | Ph-pyrazole-C$_6$H$_4$-OCH$_3$ | —C$_2$H$_4$SO$_3$H | 2.04 | >200 |
| 41* | Ph-pyrazole-C$_6$H$_4$-Cl | —C$_2$H$_4$SO$_3$H | 3.66 | >200 |
| 42 | Ph-pyrazole-C$_6$H$_4$-SO$_2$-morpholine | —C$_2$H$_4$SO$_3$H | 1.86 | 85.0 |
| 43 | Ph-pyrazole-C$_6$H$_4$-SO$_2$-piperidine | —C$_2$H$_4$SO$_3$H | 2.07 | 20.1 |
| 44 | Ph-pyrazole-Ph | sulfolanyl | >100 | >200 |
| 45 | Ph-pyrazole-C$_6$H$_4$-Cl | sulfolanyl | >100 | >200 |
| 46 | Ph-pyrazole-C$_6$H$_3$(F)-OCH$_2$CH$_3$ | —CH$_2$CO$_2$H | 3.45 | >200 |

Compounds of Tables 2-4 did not inhibit MMP-2 and MMP-9 appreciably up to 50 μM with the exception of compounds 32 (MMP-2: IC$_{50}$ 13.7 μM); 33 (MMP-2: IC$_{50}$=39.4 μM); 38 (MMP-2: IC$_{50}$=10.1 μM); 40 (MMP-2: IC$_{50}$=34.5 μM); 41 (MMP-2: IC$_{50}$=26.9 μM).

As shown in Table 2, inclusion of an oxazole or a thiazole ring generally did not result in substantially effective compounds against any of the proteases. On the contrary, the isoxazole substitution led to compounds that overall seemed to effectively inhibit LF, but not BoNT/A. However, compound 23 (Table 3) also inhibited MMP-2 in the low micromolar range. With respect to the compounds of Table 3, the furan ring was replaced with a pyrazole (Table 4) and this series was found to be most effective against LF. Two of these compounds also inhibited BoNT A in the low micromolar range. Compounds 34 and 35 displayed IC$_{50}$ values of 8.18 μM and 5.45 μM, respectively, against BoNT/A. Although these two inhibitors (compounds 34 and 35) also inhibit LF, the most potent pyrazole derivatives against LF were 40, 42, and 43 (Table 4).

Finally, the substitutions of the furan ring were explored with various other ring motifs such as indoles/thioindoles (Table 5), as well as other ring systems shown in Table 6.

TABLE 5

Rhodanine derivatives and IC$_{50}$ values against lethal factor (LF), BoTN/A, MMP-2, and MMP-9.

| Compd. | Ar | LF IC$_{50}$ (µM) | BoNT/A IC$_{50}$ (µM) | MMP2 IC$_{50}$ (µM) | MMP9 IC$_{50}$ (µM) |
|---|---|---|---|---|---|
| 47 | (2,3-dihydrothieno[3,4-b][1,4]dioxine, 5-bromo-7-methyl) | 11.4 | >200 | 50.6 | >100 |
| 48 | (5-morpholinothiophen-2-yl) | 32.5 | 112 | 47.1 | 64.9 |
| 49 | (4-biphenyl) | 6.20 | 54.6 | >100 | >100 |
| 50 | (3-pyrrolidin-1-ylphenyl) | 28.1 | >200 | >100 | >100 |
| 51 | (4-(4-methyl-1,4-diazepan-1-yl)phenyl) | >25 | >50 | >25 | >25 |
| 52 | (3-(1H-pyrazol-1-yl)phenyl) | 27.9 | >200 | >100 | >100 |
| 53 | (benzo[d][1,3]dioxol-5-yl) | 83.3 | >200 | >100 | >100 |
| 54 | (2-methylquinolin-6-yl) | 5.25 | >200 | 18.0 | >100 |
| 55 | (dibenzofuran-4-yl) | 2.96 | 160 | >100 | >100 |
| 56 | (6-bromopyridin-2-yl) | 58.0 | >200 | >100 | >100 |

TABLE 6

Structure-activity relationship of various ring motifs coupled with rhodanine acetic acid showing $IC_{50}$ values against lethal factor (LF), BoTN/A, MMP-2, and MMP-9.

| Compd. | Ar | LF $IC_{50}$ (μM) | BoNT/A $IC_{50}$ (μM) | MMP2 $IC_{50}$ (μM) | MMP9 $IC_{50}$ (μM) |
|---|---|---|---|---|---|
| 57 | 3-methylbenzothiophene | 13.0 | >200 | >100 | >100 |
| 58 | 5-bromo-3-methylbenzothiophene | 10.4 | 74.3 | 46.9 | 64.9 |
| 59 | methylthieno[2,3-b]pyrazine | 24.9 | >200 | >100 | >100 |
| 60 | 3-methylindole | 38.7 | >200 | >100 | >100 |
| 61 | 5-bromo-3-methylindole | 7.04 | >200 | >100 | >100 |
| 62 | 3-Cl-phenyl oxindole amide | 4.40 | >200 | >25 | >25 |
| 63 | 3-CH$_3$-phenyl oxindole amide | 5.71 | >200 | >100 | >100 |

While most of the indole or thioindole derivatives showed to be effective against LF, this was not the case with BoNT/A. When the furan ring was substituted with other various ring systems (Table 6), the resulting compounds lack in activity against both toxins. Using a kinetic assay, Rosiglitizone (compound 2) was also tested as a potential protease inhibitor and found that it did not appreciably inhibit LF or BoNT A (tested at 100 μM). Overall, compounds 9 and 13 are the two most potent inhibitors of LF amongst the new series with $K_i$ values of 0.1 μM and 1.0 μM, respectively (FIG. 1). Kinetic assays in the presence of PA (one component of anthrax tripartite, which binds LF and allows it to enter the cytosol) were also performed to determine if the inhibitory effect of the compounds would change in a more biological state.

Significantly effective inhibitors of the invention include the pyrazoles compounds 34 and 35, given that they inhibited both bacterial toxins, BoNT/A, and LF, but did not inhibit the human proteases MMP-2 or MMP-9.

Docking studies performed using the X-ray co-ordinates of BoNT A (PDB-ID 2G7N; 54) and LF (PDB-ID 1YQY; 55) indicate that pyrazole-rhodanine derivatives such as compound 34 are nicely positioned into the binding pocket of the enzyme, placing both the exosulfur atom of the rhodanine ring and the carboxylate group in close proximity to the zinc metal ion (FIG. 2).

To further test the druggability of the LF inhibitors of the invention, in vitro ADME-Tox (absorption, distribution, metabolic, excretion, and toxicity) studies were performed (Table 7). From these studies, it can be concluded that compounds 1 and 65 did not show any major cytotoxicity effects, are chemically stable, did not degrade in plasma, and are not rapidly metabolized by hepatocytes. It was also shown that compounds 1 and 65 had very little effect on the inhibition of the cytochrome P450s (CYPs) and the hERG receptor (Table 7). In contrast, compound 64 (Table 7), was found to inhibit CYP1A2 and showed to be metabolically unstable. In addition, compounds 9, 34, 38, 39, and 40 were shown to protect macrophages from LF/PA-induced cell death when tested at 50 and 100 μM concentration.

TABLE 7

In vitro ADME-tox experiments with selected LF compounds of the invention.

| Structure/ID | $IC_{50}$ (μM) | Chem Stab. (a) | logS Ug/ mL (b) | Cytox. (c) | Pampa (d) | Pgp (μM) (e) | CYP 2C19 $IC_{50}$ (μM) (f) | CYP 2D6 $IC_{50}$ (μM) (g) |
|---|---|---|---|---|---|---|---|---|
| 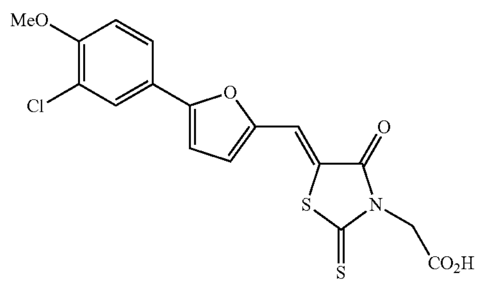  1 | 0.29 | 100% | <10 | Nontoxic up to 100 μM | ND | A | 31.3 | 30.5 |
| 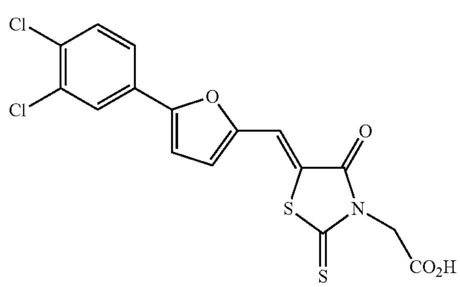  64 | 0.26 | 88% | <10 | Nontoxic up to 100 μM | Med. | A | 36.9 | 47.6 |
| 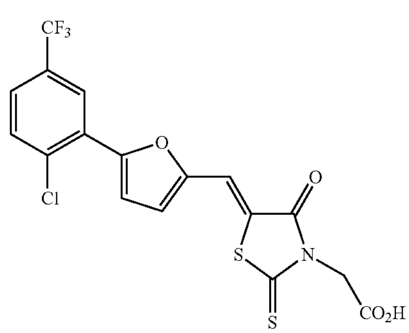  65 | 0.19 | 97% | <10 | Nontoxic up to 100 μM | ND | >100 | >100 | >100 |

TABLE 7-continued

| Structure/ID | | | | | | | |
|---|---|---|---|---|---|---|---|
| 66 | 2.3 | 85% | <10 | Nontoxic up to 100 µM | Med. | A | A | A |
| 67 | 0.32 | ND | <10 | Nontoxic up to 100 µM | Low | >100 | >100 | >50 |

| Structure/ID | CYP 1A2 IC$_{50}$ (µM) (h) | CYP 3A4 IC$_{50}$ (µM) (i) | CYP 2C9 IC$_{50}$ (µM) (j) | Met. Stab. t$_{1/2}$(min) CL$_{int}$ µl/min·10$^6$ cells (k) | Plasma Stab. T = 30 min (l) | Liver S9 Stab t$_{1/2}$(min) CL$_{int}$ µl/min·10$^6$ cells (m) | hERG % inhib. at 30 µM (n) |
|---|---|---|---|---|---|---|---|
| 1 | 20.9 | * | 28.3 | t$_{1/2}$ = 37.1 CL$_{int}$ = 21.6 | 90% | t$_{1/2}$ = 127.7 CL$_{int}$ = 5.6 | 58 |
| 64 | 2.79 | >50 | >50 | Degraded | 79% | Degraded | 67 |

TABLE 7-continued

| Compound | a | b | c | d | e | f-j | i | k | l | m | n |
|---|---|---|---|---|---|---|---|---|---|---|---|
| 65 | 20.5 | * | >100 | | | $t_{1/2}$ = 42.4 $CL_{int}$ = 19.8 | 82% | | $t_{1/2}$ = 37.3 $CL_{int}$ = 25.0 | | 45 |
| 66 | A | * | >100 | | | Degraded | 90% | | Degraded | | 29 |
| 67 | >100 | * | >100 | | | ND | ND | | ND | | 9 |

$^a$Chemical stability; $^b$The apparent (kinetic) solubility; $^c$Cytotoxicity against HepG2 cells; $^d$Cell permeability using the PAMPA method; $^e$Inhibition of P-glycoprotein-mediated transport of calcein-AM out of the cell; $^{f-j}$Evaluation of the ability of the LF compounds to inhibit human CYPs-mediated transformation of 3-cyano-7-ethoxycoumarin; $^i$Evaluation of the ability of LF inhibitors to inhibit CYP 3A4-mediated transformation of dibenzylfluorescein; $^k$Metabolic stability with rat hepatocytes; $^l$Stability in rat plasma. $^m$Metabolic stability in liver microsomes; $^n$Inhibition of the hERG channel was measured using hERG K+ radioligand; *, no dose-response curve; ND, not detected; A, compounds that had high absorbance at the wavelength used for the assay; LF, lethal factor.

Figure 3:
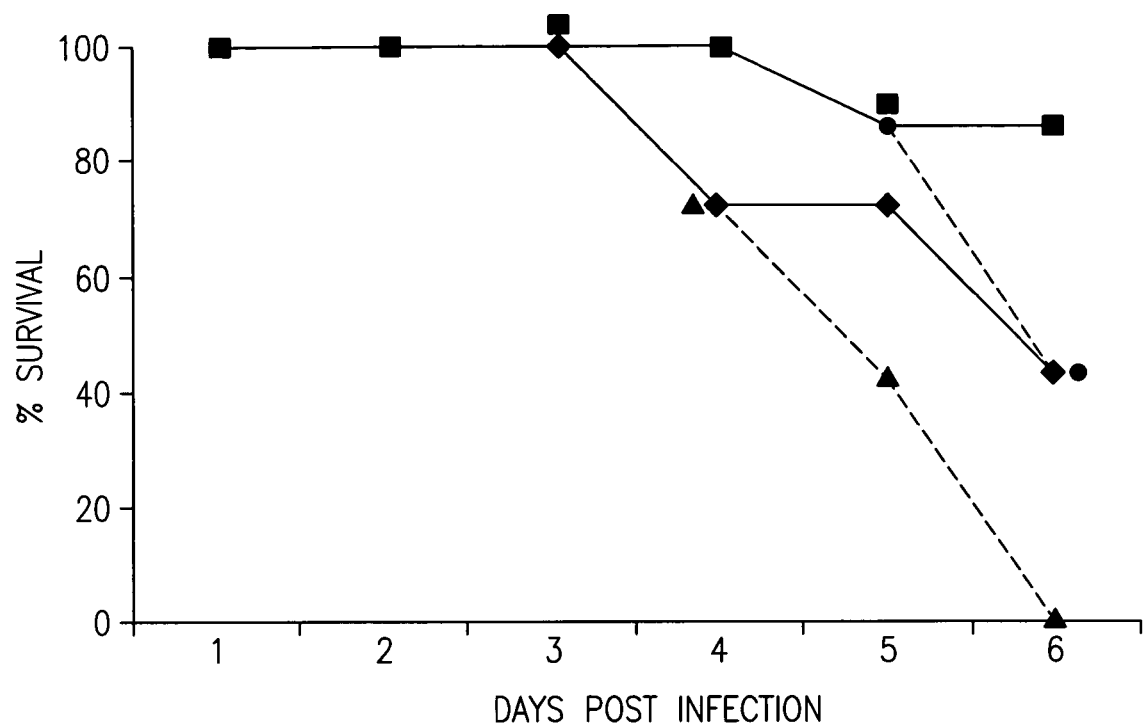
FIG. 3: Compound 34 and ciprofloxacin (cipro) protect A/J mice from anthrax. Mice (eight animals per group) were infected intranasally with 4 H $10^5$ Bacillus anthracis Sterne spores. Treatment with compound 34 (25 mg/kg in DMSO administered via intraperitoneal injection) was started 24 h postexposure and continued for the next 5 days. On the fourth day following infection, mice were given daily injections of cipro (25 mg/kg subcutaneously). Mice given DMSO alone were used as the control, and all died on day 6 (dashed line; triangles). The group treated with compound 34 and cipro (squares) had the best survival (p<0.01 compared to control group), while the group receiving compound 34 alone (dashed line; circles) also survived significantly better than control (p<0.05) and the group treated with cipro alone (diamonds).

Compound 34 was selected for in vivo efficacy studies against anthrax (FIG. 3) given its cross-reactivity with the BoNT A toxin. When administered via intraperitoneal injection, compound 34 alone or in combination with cipro protected mice against anthrax spores in which it increased survival of infected mice to >80% (FIG. 3). It is significant that these studies were done without detailed knowledge of the pharmacology of the LF inhibitors and by using a single daily dose. These data support that the rhodanine derivatives of the invention described herein are suitable for development into therapeutics against bacterial toxins.

Example 2

Preparation of Aldehyde 70

Aldehyde 70, an intermediate for the preparation of rhodanine derivative 28, was prepared as described by Tanaka et al. (*J. Med. Chem.*; 41: 2390-410).

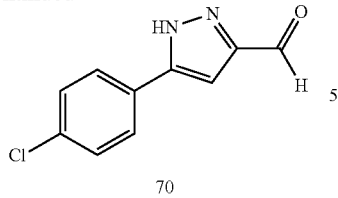

70

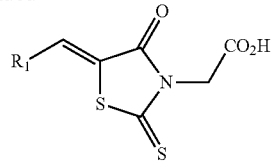

Acid 68 (0.898 mmol), HOBt (0.898 mmol) and N,O-dimethylhydroxylamine hydrochloride (0.898 mmol) were dissolved in $CH_2Cl_2$ (5 mL) and stirred for 10 min. EDC (0.898 mmol) in 5 mL of $CH_2Cl_2$ was added dropwise over 20 mins in which the colorless reaction mixture was stirred for 48 hrs. at room temperature under nitrogen. The reaction mixture was diluted with 10 mL of $CH_2Cl_2$, washed 2 times with water and twice with brine. The organic layer was dried with $Na_2SO_4$ and concentrated to give the amide 69 as a light yellow solid, which was used in the next step without further purification.

To a cooled solution of $LiAlH_4$ (0.753 mmol) in THF (5 mL) under nitrogen, compound 69 (0.376 mmol) was added dropwise and the reaction mixture was allowed to warm to room temperature over 2 hrs and was stirred overnight. The reaction mixture was cooled to 0° C. and quenched with $H_2O$, 15% NaOH and $H_2O$. It was warmed to room temperature in which $Na_2SO_4$ was added. After diluting with $Et_2O$, it was filtered and the solid was boiled in 10 mL of THF filtered and concentrated to give aldehyde 70.

This technique can be used to prepare other desired aldehydes from known or readily prepared acids, as would be readily understood by those of skill in the art.

Example 3

Preparation of Compounds of the Invention

Generic synthetic schemes and methods for the synthesis of rhodanine derivatives of the invention 17-28, 30, 32-35, 47-52, 54-59, and 61 (Tables 1-7) are provided in this Example. $R_1$ represents various heteroatoms such as furan derivatives (Tables 1 and 7), oxazole/thiazole derivatives (Table 2), isooxazole derivatives (Table 3), pyrazole derivatives (Table 4), indole/thioindole derivatives (Table 6) and other groups denoted in Table 5. Within these derivatives $R_2$ can be a carboxylic acid derivative, sulfonic acid derivative, sulfolane, or a tetrahydrofuran derivative. The variables $R_1$ and $R_2$ as used in this example can be the same or difference than other similar terms used elsewhere in the specification. Various aldehydes can be purchased from Sigma Aldrich, Acros or Astatech, Inc., or prepared by standard synthetic techniques well known to those of skill in the art.

Scheme 3.
Generic synthetic scheme for compounds listed in Tables 1-7.

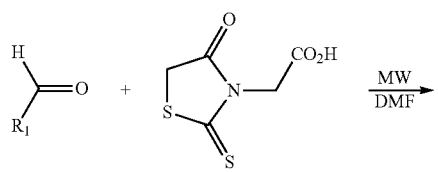

General Procedure: To a solution of the aldehyde (0.575 mmol) in N,N-dimethylformamide (DMF) (1 mL) was added rhodanine N-acetic acid (0.523 mmol) and the mixture was stirred until it became homogenous. The solution was then placed in the CEM microwave (Matthews, N.C.) for two cycles of 2 minute heating at 140° C. (ramp 2 min, 300 W) and 30 second cooling at 30° C. (ramp 2 min, 300 W). The solution was removed from the microwave and diluted with water (20 mL) and a precipitate was formed. The precipitate was collected by filtration, recrystallized using acetone/water, and was dried to give the desired compound.

2-(5-((5-furan-2-yl)isoxazol-3-yl)methylene)-4-oxo-2-thioxothiazolidin-3-yl)acetic acid (20) (0.170 g, 82.5%). $^1$H NMR (300 MHz, d-DMSO) δ 8.02 (d, 1H, J=1.5), 7.82 (d, 1H, J=1.5), 7.27 (d, 1H, J=3.6), 7.17 (d, 1H, J=1.5), 6.79 (dd, 1H, J=3.6, 1.5 Hz), 4.76 (s, 2H). MS (ESI), m/z Calcd for $C_{13}H_8N_2O_5S_2$ $[M+H]^+$ 337.0. Found: 337.0. Anal. ($C_{13}H_8N_2OS_2$) Calc.: C, 46.42; H, 2.40; N, 8.33; S, 19.07. Found: C, 46.81; H, 2.78; N, 8.44; S, 18.63.

(Z)-2-(5-((2,5-dimethyloxazol-4-yl)methylene)-4-oxo-2-thioxothiazolidin-3-yl)acetic acid (17) (0.188 g, 79%). $^1$H NMR (300 MHz, d-DMSO) δ 7.71 (s, 1H), 4.78 (s, 2H), 2.55 (s, 3H), 2.48 (s, 2H). MS (ESI), m/z Calcd for $C_{11}H_{10}N_2O_4S_2$ $[M+H]^+$ 298.01 Found: 299.1.

2-(5-((5-bromobenzo[b]thiophen-3-yl)methylene)-4-oxo-2-thioxothiazolidin-3-yl)acetic acid (58) (0.198 g, 77%). $^1$H NMR (300 MHz, d-DMSO) δ 8.54 (d, 1H, J=1.2), 8.34 (s, 1H), 8.18 (s, 1H), 8.11 (d, 1H, J=8.4), 7.67 (dd, 1H, J=1.5, 8.4), 4.78 (s, 2H). MS (ESI), m/z Calcd for $C_{14}H_8BrNO_3S_3$ $[M-H]^-$ 411.9. Found: 412.0. Anal. ($C_{14}H_8BrNO_3S_3$). Calc: C, 40.58; H, 1.95; N, 3.38; S, 23.22. Found: C, 41.12; H, 2.14; N, 3.40; S, 21.76.

2-(5-((2-methylquinolin-6-yl)methylene)-4-oxo-2-thioxothiazolidin-3-yl)acetic acid (54) (0.139 g, 69.2%, 91.0% purity by LCMS). $^1$H NMR (300 MHz, d-DMSO) δ 8.44 (d, 1H, J=8.4), 8.28 (d, 1H, J=1.8), 8.06 (s, 1H), 8.05 (d, 1H, J=8.7), 7.96 (dd, 1H, J=1.8, 8.7 Hz), 7.53 (d, 1H, J=8.7), 4.78 (s, 2H), 2.70 (s, 3H). MS (ESI), m/z Calcd for $C_{16}H_{12}N_2O_3S_2$ $[M+H]^+$ 345.0. Found: 344.9. Anal. ($C_{16}H_{12}N_2O_3S_2$) Calc: C, 55.80; H, 3.51; N, 8.13; S, 18.62. Found: C, 44.38; H, 3.38; N, 9.54; S, 20.54.

2-((5-((5-(4-chlorophenyl)-1H-pyrazol-3-yl)methylene)-4-oxo-2-thioxothiazolidin-3-yl)acetic acid (28) (0.015 g, 21%). $^1$H NMR (300 MHz, d-DMSO) δ 7.82 (d, 2H, J=7.8), 7.47 (d, 2H, J=7.8), 6.66 (s, 1H), 3.81 (s, 2H).

2-(5-((2-(1-(tert-butoxycarbonyl)piperidin-4-yl)thiazol-4-yl)methylene)-4-oxo-2-thioxothiazolidin-3-yl)acetic acid (18) (0.168 g, 73%). $^1$H NMR (300 MHz, d-DMSO) δ 8.34 (s, 1H), 7.84 (s, 1H), 4.73 (s, 2H), 4.03 (d, 2H, J=12.9), 3.28 (tt, 2H, J=3.6, 10.2), 2.96 (bs, 2H), 2.11 (dd, 2H, J=2.4, 10.2), 1.64 (dq, 2H, J=3.6, 12.6), 1.43 (s, 9H). HRMS (ESI), m/z Calcd for $C_{19}H_{23}N_3O_5S_3$ $[M+H]^+$ 470.09. Found: 470.09 Anal. ($C_{19}H_{23}N_3O_5S_3$) Calc: C, 48.60; H, 4.94; N, 8.95; S, 20.48. Found: C, 49.52; H, 4.78; N, 8.81; S, 19.25.

2-(4-oxo-5-(thieno[2,3-b]pyrazin-6-ylmethylene)-2-thioxothiazolidin-3-yl)acetic acid (59) (0.242 g, 81%). $^1$H NMR (300 MHz, d-DMSO) δ 8.89 (d, 1H, J=2.4), 8.71 (d, 1H, J=2.4), 8.34 (s, 1H), 8.39 (s, 1H), 4.78 (s, 2H). HRMS (ESI), m/z Calcd for $C_{12}H_7N_3O_3S_3$ [M+H]$^+$ 336.97. Found 337.97 Anal ($C_{12}H_7N_3O_3S_3$) Calc: C, 42.72; H, 2.09; N, 12.45; S, 28.51. Found: C, 43.04; H, 2.42; N, 12.25; S, 27.66.

2-(5-(3-(1H-pyrazol-1-yl)benzylidene)-4-oxo-2-thioxothiazolidin-3-yl)acetic acid (52) (0.136 g, 56%). $^1$H NMR (300 MHz, d-DMSO) δ 8.59 (d, 1H, J=2.7), 8.19 (s, 1H), 7.97 (td, 1H, J=0.9, 8.1), 7.96 (s, 1H), 7.83 (d, 1H, J=0.6), 7.69 (t, 1H, J=7.8), 7.58 (d, 1H, J=7.8), 6.61 (t, 1H, J=2.4), 4.77 (s, 2H). HRMS (ESI), m/z Calcd for $C_{15}H_{11}N_3O_3S_2$ [M+H]$^+$ 346.03. Found 346.03 Anal. ($C_{15}H_{11}N_3O_3S_2$) Calc: C, 52.16; H, 3.21; N, 12.17; S, 18.57. Found: C, 51.39; H, 3.33; N, 12.00; S, 17.98.

2-(5-((5-(4-methoxyphenyl)isoxazol-3-yl)methylene)-4-oxo-2-thioxothiazolidin-3-yl)acetic acid (23) (0.338 g, 73%). $^1$H NMR (300 MHz, d-DMSO) δ 7.93 (d, 2H, J=9.3), 7.76 (s, 1H), 7.17 (s, 1H), 7.16 (d, 2H, J=9.3), 4.93 (s, 2H), 3.93 (s, 3H) HRMS (ESI), m/z Calcd for $C_{16}H_{12}N_2O_5S_2$ [M+H]$^+$ 377.03. Found 377.03.

2-(4-oxo-2-thioxo-5-((5-p-tolylisoxazol-3-yl)methylene)thiazolidin-3-yl)acetic acid (22) (0.385 g, 80%). $^1$H NMR (300 MHz, d-DMSO) δ 7.82 (dd, 1H, J=8.4), 7.80 (s, 1H), 7.40 (d, 1H, J=8.1), 7.34 (s, 1H), 4.76 (s, 2H), 2.39 (s, 3H) HRMS (ESI), m/z Calcd for $C_{16}H_{12}N_2O_4S_2$ [M+H]$^+$ 361.0311. Found 377.0309. Anal. ($C_{16}H_{12}N_2O_4S_2$) C, 53.32; H, 3.36; N, 7.77; S, 17.79 Found: C, 52.93; H, 3.77; N, 7.98; S, 16.62.

2-(5-((5-(4-chlorophenyl)isoxazol-3-yl)methylene)-4-oxo-2-thioxothiazolidin-3-yl)acetic acid (24) (0.113 g, 62%). $^1$H NMR (300 MHz, d-DMSO) δ 7.97 (d, 2H, J=8.4), 7.81 (s, 1H), 7.67 (d, 2H, J=8.4), 7.45 (s, 1H), 4.76 (s, 2H). HRMS (ESI), m/z Calcd for $C_{15}H_9ClN_2O_4S_2$ [M+H]$^+$ 380.97. Found 380.98. Anal. ($C_{15}H_9ClN_2O_4S_2$) C, 47.31; H, 2.38; N, 9.31; S, 16.84 Found: C, 46.76; H, 2.75; N, 7.42; S, 16.09.

2-(5-((5-(4-fluorophenyl)isoxazol-3-yl)methylene)-4-oxo-2-thioxothiazolidin-3-yl)acetic acid (25) (0.170 g, 89%). $^1$H NMR (300 MHz, d-DMSO) δ 8.00 (dd, 1H, J=8.7, 5.4), 7.81 (s, 1H), 7.44 (t, 2H, J=8.7), 7.39 (s, 1H), 4.76 (s, 2H). HRMS (ESI), m/z Calcd for $C_{15}H_9FN_2O_4S_2$ [M+H]$^+$ 365.00. Found 365.00. Anal. ($C_{15}H_9FN_2O_4S_2$) C, 49.44; H, 2.59; N, 7.69; S, 17.60 Found: C, 49.37; H, 2.73; N, 7.87; S, 17.09.

2-(5-((1-(2,4-difluorophenyl)-3-(pyridin-3-yl)-1H-pyrazol-4-yl)methylene)-4-oxo-2-thioxothiazolidin-3-yl)acetic acid (32) (0.228 g, 95%). $^1$H NMR (300 MHz, d-DMSO) δ 8.89 (d, 1H, J=2.1), 8.80 (s, 1H), 8.75 (d, 1H, J=4.5), 8.13 (d, 1H, J=7.8), 8.00 (m, 1H), 7.70 (dt, 1H, J=2.7, 9.0), 7.64 (d, 1H, J=4.8), 7.62 (t, 1H, J=2.1), 7.37 (tt, 1H, J=2.7, 7.8), 4.74 (s, 2H). HRMS (ESI), m/z Calcd for $C_{20}H_{12}F_2N_4O_3S_2$ [M+H]$^+$ 459.04. Found: 459.04. Anal. ($C_{20}H_{12}F_2N_4O_3S_2$) C, 52.40; H, 2.64; N, 12.22; S, 13.99. Found: C, 51.67; H, 2.92; N, 12.19; S, 12.98.

2-(5-((1,3-diphenyl-1H-pyrazol-4-yl)methylene)-4-oxo-2-thioxothiazolidin-3-yl)acetic acid (30) (0.224 g, 88%). $^1$H NMR (300 MHz, d-DMSO) δ 8.89 (s, 1H), 8.11 (d, 2H, J=8.7), 7.67 (m, 8H), 7.56 (s, 1H), 4.74 (s, 2H). HRMS (ESI), m/z Calcd for $C_{21}H_{15}N_3O_3S_2$ [M+H]$^+$ 422.06. Found: 422.06. Anal. ($C_{21}H_{15}N_3O_3S_2$) C, 59.84; H, 3.59; N, 9.97; S, 15.21. Found: C, 60.04; H, 4.06; N, 10.10; S, 14.81.

2-(5-((1,3-bis(4-chlorophenyl)-1H-pyrazol-4-yl)methylene)-4-oxo-2-thioxothiazolidin-3-yl)acetic acid (34) (0.220 g, 95%). $^1$H NMR (300 MHz, d-DMSO) δ 8.90 (s, 1H), 8.12 (d, 2H, J=8.4), 7.67 (m, 6H), 7.56 (s, 1H), 4.74 (s, 2H). HRMS (ESI), m/z Calcd for $C_{21}H_{13}Cl_2N_3O_3S_2$ [M+H]$^+$ 489.98. Found: 489.98.

2-(5-((5-(4-bromophenyl)isoxazol-3-yl)methylene)-4-oxo-2-thioxothiazolidin-3-yl)acetic acid (26) (0.133, 79%). $^1$H NMR (300 MHz, d-DMSO) δ 7.90 (m, 2H, J=8.4), 7.81 (d, 2H, J=7.5), 7.78 (s, 1H), 7.47 (s, 1H), 4.77 (s, 2H). HRMS (ESI), m/z Calcd for $C_{15}H_9BrN_2O_4S_2$ [M+H]$^+$ 424.93. Found: 424.93. Anal. ($C_{15}H_9BrN_2O_4S_2$) C, 42.36; H, 2.13; N, 6.59; S, 15.08. Found: C, 42.16; H, 2.50; N, 6.61; S, 14.46.

2-(5-((1,3-bis(4-bromophenyl)-1H-pyrazol-4-yl)methylene)-4-oxo-2-thioxothiazolidin-3-yl)acetic acid (35) (0.170, 80%). $^1$H NMR (300 MHz, d-DMSO) δ 8.91 (s, 1H), 8.06 (d, 2H, J=8.7), 7.80 (d, 2H, J=6.0), 7.77 (d, 2H, J=6.6), 7.63 (d, 2H, J=8.4), 7.57 (s, 1H), 4.74 (s, 2H). HRMS (ESI), m/z Calcd for $C_{21}H_{13}Br_2N_3O_3S_2$ [M+H]$^+$ 577.88. Found: 577.88. Anal. ($C_{21}H_{13}Br_2N_3O_3S_2$) C, 43.54; H, 2.26; N, 7.25; S, 11.07. Found: C, 43.65 H, 1.77; N, 7.83; S, 10.02.

2-(5-((1,3-bis(4-fluorophenyl)-1H-pyrazol-4-yl)methylene)-4-oxo-2-thioxothiazolidin-3-yl)acetic acid (33) (0.234 g, 97%). $^1$H NMR (300 MHz, d-DMSO) δ 8.87 (s, 1H), 8.12 (dd, 2H, J=4.5, 9.0), 7.73 (d, 2H, J=5.4), 7.57 (s, 1H), 7.44 (t, 4H, J=9.0). HRMS (ESI) m/z Calcd for $C_{21}H_{13}F_2N_3O_3S_2$ [M+H]$^+$ 458.04. Found: 458.04. Anal. ($C_{21}H_{13}F_2N_3O_3S_2$) C, 55.13; H, 2.86; N, 9.19; S, 14.02. Found: C, 60.87; H, 3.11; N, 10.18; S, 13.59.

2-(5-((5-morpholinothiophen-2-yl)methylene)-4-oxo-2-thioxothiazolidin-3-yl)acetic acid (48) (0.0129 g, 5%). $^1$H NMR (300 MHz, d-DMSO) δ 7.91 (s, 1H), 7.59 (d, 1H, J=4.8), 6.48 (d, 2H, J=4.5), 4.87 (s, 2H), 3.87 (t, 4H, J=4.5), 3.48 (t, 4H, J=4.8). HRMS (ESI) m/z Calcd for $C_{14}H_{14}N_2O_4S_3$ [M+H]$^+$ 371.02. Found: 371.02. Anal. ($C_{14}H_{14}N_2O_4S_3$), C, 45.39; H, 3.81; N, 7.56; S, 25.97. Found: C, 45.26; H, 3.99; N, 6.92; S, 23.77.

2-(5-((4-(4-methyl-1,4-diazepan-1-yl)benzylidene)-4-oxo-2-thioxothiazolidin-3-yl)acetic acid (51) (0.218 g, 81%). $^1$H NMR (300 MHz, d-DMSO) δ 7.74 (s, 1H), 7.52 (d, 2H, J=8.7), 6.93 (d, 2H, J=9.0), 4.64 (s, 2H), 3.70 (m, 2H), 3.57 (t, 2H, J=6.0), 2.83 (m, 2H), 3.68 (m, 2H), 2.42 (s, 3H), 1.99 (m, 2H) HRMS (ESI), m/z Calcd for $C_{18}H_{21}N_3O_3S_2$ [M+H]$^+$ 392.1097 Found: 392.1092.

2-(5-((2-methyl-4-phenylthiazol-5-yl)methylene)-4-oxo-2-thioxothiazolidin-3-yl)acetic acid (19) (0.206 g, 74%). $^1$H NMR (300 MHz, d-DMSO) δ 7.81 (s, 1H), 7.65-7.68 (m, 2H), 7.60-7.56 (m, 3H), 4.72 (s, 2H), 2.84 (s, 3H). HRMS (ESI), m/z Calcd for $C_{16}H_{12}N_2O_3S_3$ [M+H]$^+$ 377.01. Found: 377.01 Anal. ($C_{16}H_{12}N_2O_3S_3$) C, 51.05; H, 3.21; N, 7.44; S, 25.55. Found: C, 50.88; H, 3.29; N, 7.60; S, 24.99.

2-(5-((D-(4-chlorophenyl)-1H-pyrazole-3-yl)methylene)-4-oxo-2-thioxothiazolidin-3-yl)acetic acid (27) (0.198 g, 74%). $^1$H NMR (300 MHz, d-DMSO) δ 8.45 (br.s., 1H), 7.94 (d, 2H, J=8.0 Hz), 7.83 (d, 2H, J=8.0 Hz), 7.64 (s, 1H), 4.73 (s, 2H). HRMS (ESI) m/z Calcd for $C_{16}H_{12}N_2O_3S_3$ [M+H]$^+$ 414.01. Found: 414.01.

2-(5-((7-bromo-2,3-dihydrothieno[3,4-b][1,4]dioxin-5-yl)methylene)-4-oxo-2-thioxothiazolidin-3-yl)acetic acid (47) (0.208 g, 82%). $^1$H NMR (300 MHz, d-DMSO) δ 7.71 (s, 1H), 4.71 (s, 2H), 4.47 (d, 2H, J=4.8), 4.42 (d, 2H, J=3.9). HRMS (ESI), m/z Calcd for $C_{12}H_8BrNO_5S_3$ [M+H]$^+$ 421.88. Found: 421.88.

2-(4-oxo-5-((2-(pyrrolidin-1-yl)pyridin-4-yl)methylene)-2-thioxothiazolidin-3-yl)acetic acid (50) (0.157 g, 53%). $^1$H NMR (300 MHz, d-$C_2H_6$O) δ 8.27 (d, 1H, J=5.0), 7.73 (s, 1H), 6.73 (dd, 1H, J=1.5, 5.0), 6.63 (d, 1H, J=1.5), 4.92 (s, 2H), 3.53 (t, 4H, J=6.6), 1.32 (m, 4H). HRMS (ESI), m/z Calcd for $C_{15}H_{15}N_3O_3S_2$ [M+H]$^+$ 350.06. Found: 350.06.

2-(5-(benzo[c]thiophen-1-ylmethylene)-4-oxo-2-thioxothiazolidin-3-yl)acetic acid (57) (0.215 g, 81%) $^1$H NMR (300 MHz, d-DMSO) δ 8.28 (s, 1H), 8.21 (d, 1H, J=7.2), 8.14 (d, 1H, J=6.6), 8.12 (s, 1H), 7.54 (m, 2), 4.78 (s, 2H). HRMS (ESI), m/z Calcd for $C_{14}H_9NO_3S_3$ [M+H]$^+$ 335.98. Found: 335.98.

2-5-((6-bromopyridin-2-yl)methylene)-4-oxo-2-thioxothiazolidin-3-yl)acetic acid (56) (0.252 g, 87%). $^1$H NMR (300 MHz, d-DMSO) δ 8.02 (d, 1H, J=7.5), 7.95 (t, 1H, J=7.8), 7.91 (s, 1H), 7.5 (d, 1H, J=7.8), 4.76 (s, 2H) HRMS (ESI), m/z Calcd for $C_{11}H_7BrN_2O_3S_2$ [M+H]$^+$ 358.92. Found: 358.52. Anal. ($C_{11}H_7BrN_2O_3S_2$) C, 36.78; H, 1.96; N, 7.80; S, 17.85 Found: C, 37.06; H, 1.92; N, 8.04; S, 17.19.

2-(5-(dibenzo[b,d]furan-3-ylmethylene)-4-oxo-2-thioxothiazolidin-3-yl)acetic acid (55) (0.030 g, 10%). $^1$H NMR (300 MHz, d-DMSO) δ 8.38 (d, 1H, J=7.5), 8.25 (dist.d, 3H), 7.89 (d, 1H, J=8.4), 7.72 (d, 1H, J=7.8), 7.62 (m, 2H), 7.50 (t, 1H, J=7.5), 4.80 (s, 2H) HRMS (ESI), m/z Calcd for $C_{18}H_{11}NO_4S_2$ [M+H]$^+$ 370.02. Found: 370.02. Anal. ($C_{18}H_{11}NO_4S_2$) C, 58.52; H, 3.00; N, 3.79; S, 17.37 Found: C, 58.79; H, 3.10; N, 3.99, S, 16.04.

2-(5-((5-bromoindolin-2-yl)methylene)-4-oxo-2-thioxothiazolidin-3-ylo)acetic acid (61) (0.147 g, 55%). $^1$H NMR (300 MHz, d-DMSO) δ 8.30 (s, 1H), 8.20 (s, 1H), 7.99 (d, 1H, J=2.7), 7.49 (d, 1H, J=8.4), 7.40 (d, 1H, J=8.7), 4.74 (s, 2H). HRMS (ESI), m/z Calcd for $C_{14}H_{11}BrN_2O_3S_2$ [M+H]$^+$ 396.93. Found: 396.93. Anal. ($C_{14}H_{11}BrN_2O_3S_2$) C, 42.33; H, 2.28; N, 7.05; S, 16.14 Found: C, 40.79; H, 2.46; N, 6.97; S, 15.03.

2-(4-oxo-2-thioxo-5-((5-phenylisoxazol-3-yl)methylene) thiazolidin-3-yl)acetic acid (21) (0.136 g, 75%). $^1$H NMR (300 MHz, d-DMSO) δ 7.94 (m, 2H), 7.81 (s, 1H), 7.60 (m, 3H), 7.41 (s, 1H), 4.76 (s, 2H). HRMS (ESI), m/z Calcd for $C_{15}H_{10}N_2O_4S_2$ [M+H]$^+$ 347.0155. Found: 347.0157. Anal. ($C_{15}H_{10}N_2O_4S_2$) C, 52.01; H, 2.91; N, 8.09; S, 18.51. Found: C, 52.13; H, 3.38; N, 9.30; S, 15.93.

2-(5-biphenyl-4-ylmethylene-4-oxo-2-thioxothiazolidin-3-yl)acetic acid (49) (0.071 g, 38.4%). $^1$H NMR (300 MHz, d-DMSO) δ 7.97 (s, 1H), 7.90 (d, 2H, J=8.1 Hz), 7.80 (d, 4H, J=8.1 Hz), 7.52 (t, 2H, J=7.2, Hz), 7.45 (d, 1H, J=7.2 Hz) 4.76 (s, 2H). HRMS (ESI), m/z Calcd for $C_{18}H_{13}NO_3S_2$ [M+H]$^+$ 356.0410. Found: 356.0409. Anal. ($C_{18}H_{13}NO_3S_2$) C, 60.83; H, 3.69; N, 3.94; S, 18.04 Found: C, 61.17; H, 3.72; N, 4.18; S, 17.22.

CITED DOCUMENTS

1. Leppla S. H. (1982) Proc Natl Acad Sci USA; 79:3162-3166.
2. Vitale G. et al. (1998) Biochem Biophys Res Commun; 248:706-711.
3. Duesbery N. S. et al. (1998) Science; 280:734-737.
4. Park J. M. et al. (2002) Science; 297:2048-2051.
5. Forino M. et al. (2005) Proc Natl Acad Sci USA; 102:9499-9504.
6. Johnson S. L. et al. (2006) J Med Chem; 49:27-30.
7. Paddle B. M. (2003) J Appl Toxicol; 23:139-170.
8. Burnett J. C. et al. (2005) Nat Rev Drug Discov; 4:281-297.
9. Lipozencic J. et al. (2006) Acta Dermatovenerol Croat; 14:61.
10. Marks J. D. (2004) Anesthesiol Clin North America; 22:509-532, vii.
11. Montecucco C. et al. (2005) Curr Opin Pharmacol; 5:274-279.
12. Cheng C. M. et al. (2006) Am J Health Syst Pharm; 63:225-232.
13. Cheng C. M. et al. (2006) Am J Health Syst Pharm; 63:145-152.
14. Burnett J. C. et al. (2007) J Biol Chem; 282:5004-5014
15. Meunier F. A. et al. (2003) Mol Cell Neurosci; 22:454-466.
16. Lacy D. B. et al. (1998) Nat Struct Biol; 5:898-902.
17. Dong M. et al. (2006) Science; 312:592-596.
18. Singh B. R. (2000) Nat Struct Biol; 7:617-619.
19. Binz T. et al (1994) J Biol Chem; 269:1617-1620.
20. Schiavo G. et al. (1992) Nature; 359:832-835.
21. Rossetto O. et al. (1994) Nature; 372:415-416.
22. Schiavo G. et al. (1993) J Biol Chem; 268:23784-23787.
23. Schiavo G. et al. (1993) J Biol Chem; 268:11516-11519.
24. Blasi J. et al. (1993) EMBO J; 12:4821-4828.
25. Burnett J. C. et al. (2007) J Med Chem; 50:2127-2136.
26. Deshpande S. S. et al. (1997) Toxicon; 35:433-445.
27. Sheridan R. E. et al. (1997) Toxicon; 35:1439-1451.
28. Tang J. et al. (2007) PLoS ONE; 2:e761.
29. Silvaggi N. R. et al. (2007) Chem Biol; 14:533-542.
30. Sing W. T. et al. (2001) Bioorg Med Chem Lett; 11:91-94.
31. Fujishima H. et al. (2002) Br J Ophthalmol; 86:860-863.
32. Grant E. B. et al. (2000) Bioorg Med Chem Lett; 10:2179-2182.
33. Sim M. M. et al. (2002) Bioorg Med Chem Lett; 12:697-699.
34. Whitesitt C. A. et al. (1996) Bioorg Med Chem Lett; 6:2157-2162.
35. Degterev A. et al. (2001) Nat Cell Biol; 3:173-182.
36. Desai K. G. et al. (2006) J Saudi Chem Soc; 9:631-639.
37. Desai K. G. et al. (2006) J Sulfur Chem; 27:315-328.
38. Abdel-Halim A. M. et al. (1994) Indian J Heterocycl Chem; 4:45-50.
39. Pachhamia V. L. et al. (1991) Acta Cienc Indica Chem; 17C:67-78.
40. Ashour F. A. et al. (1993) Bull Fac Pharm (Cairo Univ); 31:381-386.
41. Bapodra A. H. et al. (2002) Indian J Pharm Sci; 64:501-504.
42. Zapadnyuk V. I. (1966) Vrach Delo; 10:71-75.
43. Zapadnyuk V. I. (1962) Farm Zh (Kiev); 17:36-41.
44. Momose Y. et al. (1991) Chem Pharm Bull (Tokyo); 39:1440-1445.
45. Sortino M. et al. (2007) Bioorg Med Chem; 15:484-494.
46. Saghatelian A. et al. (2004) Proc Natl Acad Sci USA; 101:10000-10005.
47. Wu C. C. et al. (2007) Proc Natl Acad Sci USA; 104:3990-3995.
48. Sabet M. et al. (2006) FEMS Immunol Med Microbiol; 47:369-379.
49. Shiryaev S. A. et al. (2007) J Biol Chem; 282:20847-20853.
50. Jones G. et al. (1995) J Mol Biol; 245:43-53.
51. Jones G. et al. (1997) J Mol Biol; 267:727-748.
52. Eldridge M. D. et al. (1997) J Comput Aided Mol Des; 11:425-445.
53. Teschner M. et al. (1994) J Mol Graphics; 12:98-105.
54. Fu Z. et al. (2006) Biochemistry; 45:8903-8911.
55. Shoop W. L. et al. (2005) Proc Natl Acad Sci USA; 102:7958-7963.
56. Pearlman R. S. (1998) Concord, distributed by Tripos (St Louis).
57. Johnson S. L. et al. (2007) Bioorg Chem; 35:306-312.
58. Lipinski C. A. et al. (2001) Adv Drug Deliv Rev; 46:3-26.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula I:

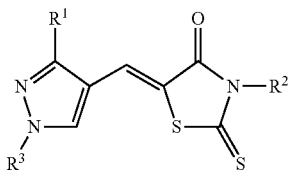

(I)

wherein

R$^1$ is phenyl, pyridyl, or thiophenyl optionally substituted with 1, 2, or 3 substituents independently selected from halo, C$_{1-3}$alkyl, C$_{1-3}$alkoxy, (aryl)C$_{1-3}$alkoxy optionally substituted with halo, —CF$_3$, —NO$_2$, —CO$_2$H, —SO$_2$NH$_2$, —SO$_2$NR$^x$R$^y$ wherein R$^x$ and R$^y$ taken together with the nitrogen to which they are attached form a morpholino or piperidino group, or an ortho fused tetrahydrofuran optionally substituted with C$_{1-3}$alkyl;

R$^2$ is —CH$_2$CO$_2$H, —(CH$_2$)$_{1-3}$SO$_3$H, or heterocycle;

wherein any CH$_2$ or heterocycle of R$^2$ is optionally substituted with 1 or 2 substituents independently selected from halo, —OR$^a$, —NO$_2$, —NH$_2$, —SO$_2$NH$_2$, —CO$_2$H, —CONH$_2$, —CO$_2$CH$_3$, —OCF$_3$, or —CF$_3$; wherein R$^a$ is hydrogen, or C$_{1-4}$alkyl; and R$^3$ is phenyl optionally substituted with 1-5 halo groups;

or a pharmaceutical acceptable salt thereof.

2. The compound of claim 1 wherein the compound is:

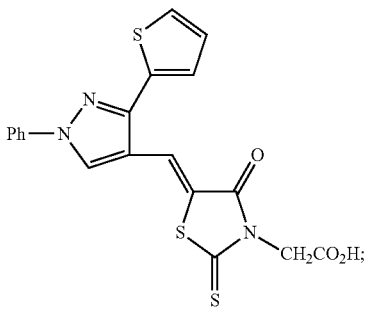

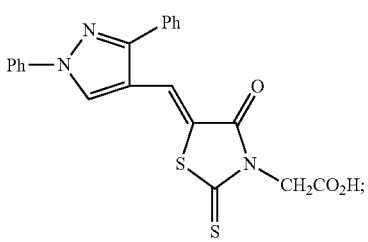

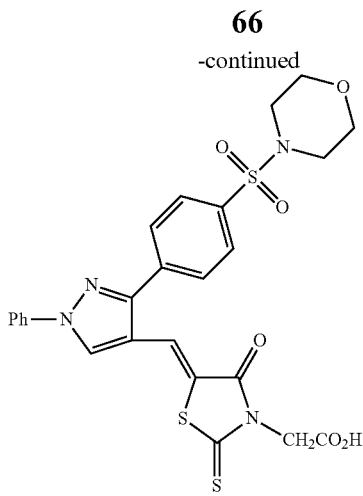

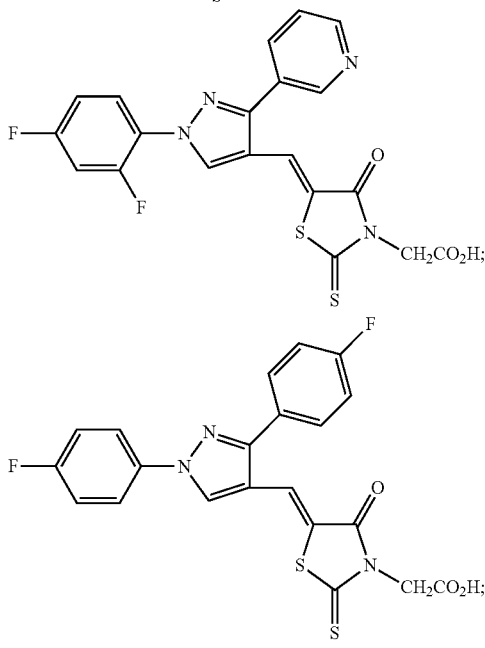

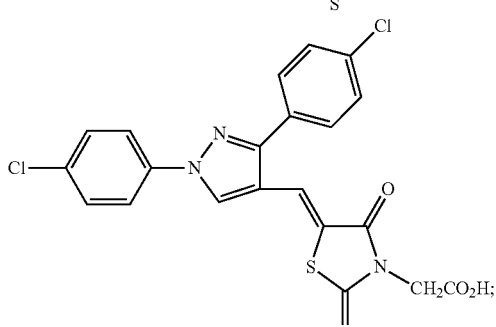

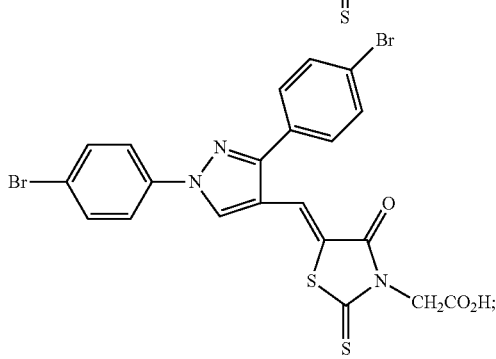

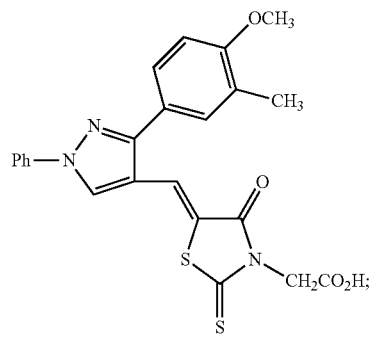
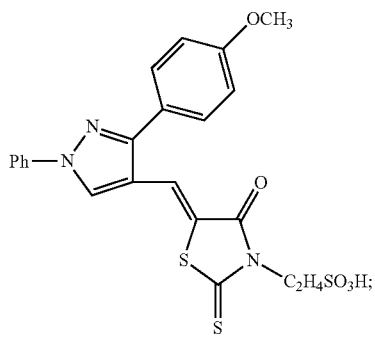
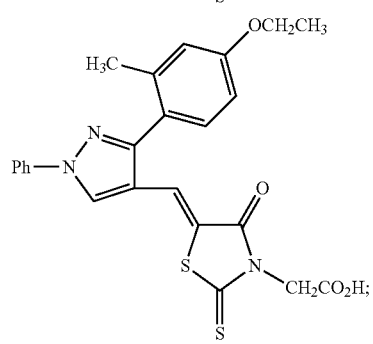
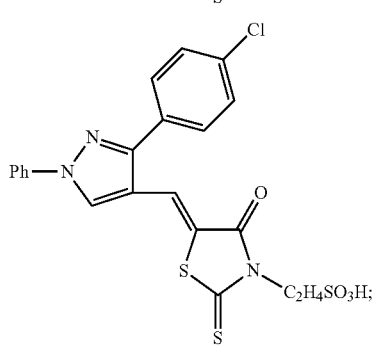
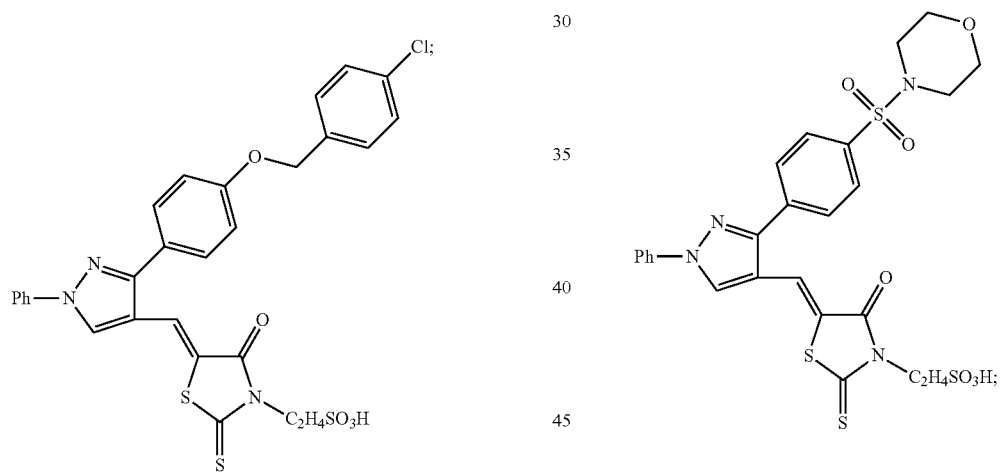
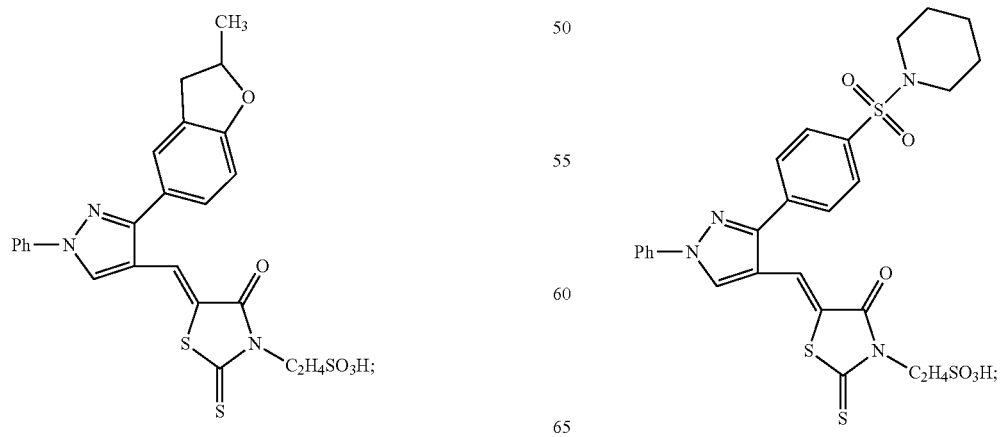

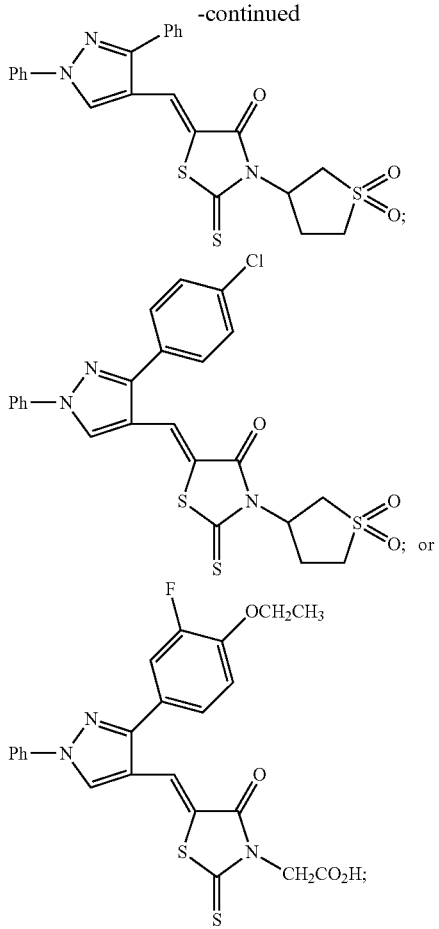

or a pharmaceutical acceptable salt thereof.

3. A therapeutic method comprising inhibiting lethal factor protease in a mammal in need of such therapy, by administering an effective inhibitory amount of a compound of formula I:

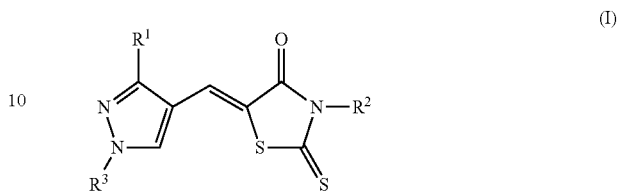

wherein
- $R^1$ is phenyl, pyridyl, or thiophenyl optionally substituted with 1, 2, or 3 substituents independently selected from halo, $C_{1-3}$alkyl, $C_{1-3}$alkoxy, (aryl)$C_{1-3}$ alkoxy optionally substituted with halo, —$CF_3$, —$NO_2$, —$CO_2H$, —$SO_2NH_2$, —$SO_2NR^xR^y$ wherein $R^x$ and $R^y$ taken together with the nitrogen to which they are attached form a morpholino or piperidino group, or an ortho fused tetrahydrofuran optionally substituted with $C_{1-3}$ alkyl;
- $R^2$ is —$CH_2CO_2H$, $(CH_2)_{1-3}SO_3H$, or heterocycle;
  wherein any $CH_2$ or heterocycle of $R^2$ is optionally substituted with 1 or 2 substituents independently selected from halo, —$OR^a$, —$NO_2$, —$NH_2$, —$SO_2NH_2$, —$CO_2H$, —$CONH_2$, —$CO_2CH_3$, —$OCF_3$, or —$CF_3$;
  wherein $R^a$ is hydrogen, or $C_{1-4}$alkyl; and
- $R^3$ is phenyl optionally substituted with 1-5 halo groups;

or a pharmaceutical acceptable salt thereof.

4. The method of claim 3 wherein the compound is administered in combination with an antibacterial agent.

5. The method of claim 4 wherein the antibacterial agent is ciprofloxacin.

* * * * *

UNITED STATES PATENT AND TRADEMARK OFFICE
CERTIFICATE OF CORRECTION

PATENT NO. : 7,947,717 B2
APPLICATION NO. : 12/176058
DATED : May 24, 2011
INVENTOR(S) : Maurizio Pellecchia It is certified that error appears in the above-identified patent and that said Letters Patent is hereby corrected as shown below:

On the Title page, in field (56), under "Other Publications", in column 1, line 10, delete "Boulamwini," and insert -- Buolamwini, --, therefor.

On the Title page, in field (56), under "Other Publications", in column 2, line 44, delete "USAA," and insert -- USA, --, therefor.

In column 65, line 27, in Claim 1, delete "-SO$_2$NR$^X$R$^Y$" and insert -- -SO$_2$NR$^x$R$^y$ --, therefor.

In column 67, lines 31-46, in Claim 2, delete

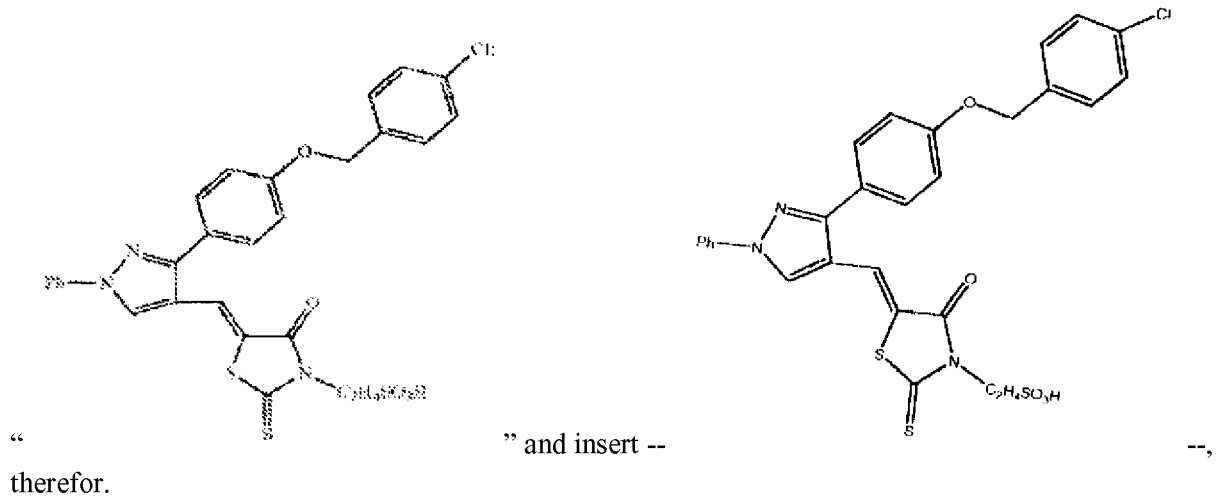

" and insert -- --, therefor.

In column 70, line 19, in Claim 3, delete "(aryl)C$_{1-3}$ alkoxy" and insert -- (aryl)C$_{1-3}$alkoxy --, therefor.

In column 70, line 21, in Claim 3, delete "-SO$_2$NR$^X$R$^Y$" and insert -- -SO$_2$NR$^x$R$^y$ --, therefor.

In column 70, line 23, in Claim 3, delete "C$_{1-3}$ alkyl;" and insert -- C$_{1-3}$alkyl; --, therefor.

Signed and Sealed this
Twelfth Day of July, 2011

David J. Kappos
*Director of the United States Patent and Trademark Office*

In column 70, line 24, in Claim 3, delete "$(CH_2)_{1-3}SO_3H$," and insert -- $-(CH_2)_{1-3}SO_3H$, --, therefor.